United States Patent [19]

Doi et al.

[11] Patent Number: 5,058,603
[45] Date of Patent: Oct. 22, 1991

[54] LENGTH-MEASURING DEVICE AND REFERENCE COLOR DISPLAY DEVICE FOR COLOR TONE ADJUSTMENT FOR USE IN COMBINATION WITH ENDOSCOPE

[75] Inventors: Yuzuru Doi; Hiroshi Shirahata; Kunio Takahashi, all of Tokyo, Japan

[73] Assignee: Asahi Kogaku Kogyo K.K., Tokyo, Japan

[21] Appl. No.: 386,477

[22] Filed: Jul. 28, 1989

[30] Foreign Application Priority Data

| Aug. 9, 1988 | [JP] | Japan | 63-199193 |
| Aug. 29, 1988 | [JP] | Japan | 63-215863 |
| Sep. 19, 1988 | [JP] | Japan | 63-235780 |
| Sep. 19, 1988 | [JP] | Japan | 63-235781 |
| Sep. 19, 1988 | [JP] | Japan | 63-235782 |
| Oct. 24, 1988 | [JP] | Japan | 63-269092 |
| Nov. 21, 1988 | [JP] | Japan | 63-294014 |
| Nov. 21, 1988 | [JP] | Japan | 63-294015 |
| Apr. 27, 1989 | [JP] | Japan | 63-50485 |
| May 18, 1989 | [JP] | Japan | 63-125441 |

[51] Int. Cl.$^5$ ............................................. A61B 5/103
[52] U.S. Cl. ............................................. 128/774
[58] Field of Search .................. 128/774, 778, 780; 33/511, 512, 700

[56] References Cited

U.S. PATENT DOCUMENTS

| 4,072,144 | 2/1978 | Pelosi et al. | 128/774 |
| 4,362,167 | 12/1982 | Nicolai et al. | 33/512 |
| 4,428,385 | 1/1984 | Morales | 128/774 |
| 4,685,474 | 8/1987 | Kurz et al. | 33/512 |
| 4,863,423 | 9/1989 | Wallace | 128/774 |

FOREIGN PATENT DOCUMENTS

| 510230 | 12/1974 | U.S.S.R. | 128/780 |
| 0736949 | 5/1980 | U.S.S.R. | 128/780 |

Primary Examiner—Lee S. Cohen
Assistant Examiner—K. M. Pfaffle
Attorney, Agent, or Firm—Sughrue, Mion, Zinn, Macpeak & Seas

[57] ABSTRACT

A length-measuring device comprises a flexible tube having a first slit and a second slit disposed rearwardly of the first slit, said tube being bendable at each of the first and second slit, and said tube further having a length-measuring portion extending forwardly from the first slit to a distal end of said tube; and means for bending said tube at the first and second slits. Typically, the bending means is a wire which has a connection relation with the length-measuring portion to pull the same. The length-measuring portion is coated with regularly arranged scale marks. After being projected from a forceps channel of an endoscope, the length-measuring portion is pulled to assume a T-shape. The length-measuring portion can be disposed at the center of a field of vision of the endoscope, and also can be easily brought into intimate contact with a target affected part. In a reference color display device, the length-measuring portion is replaced by a distal end portion coated with three primary colors.

77 Claims, 27 Drawing Sheets

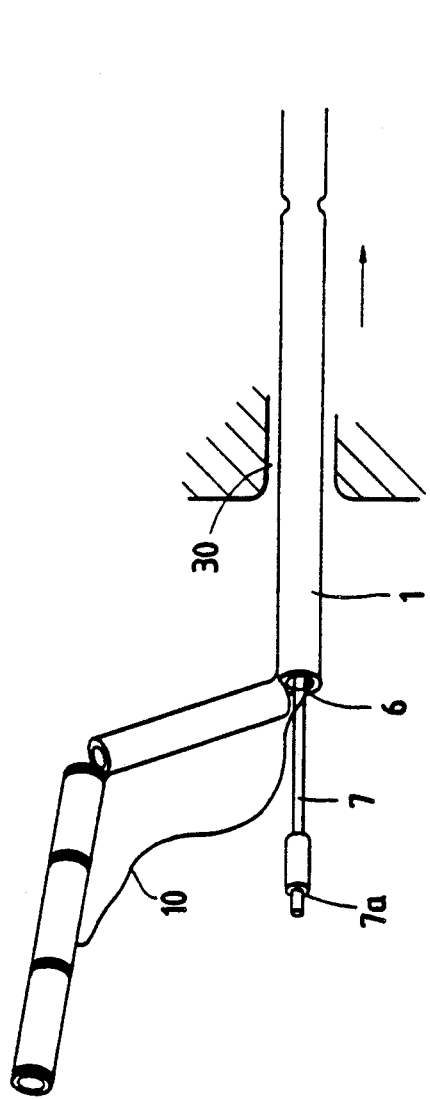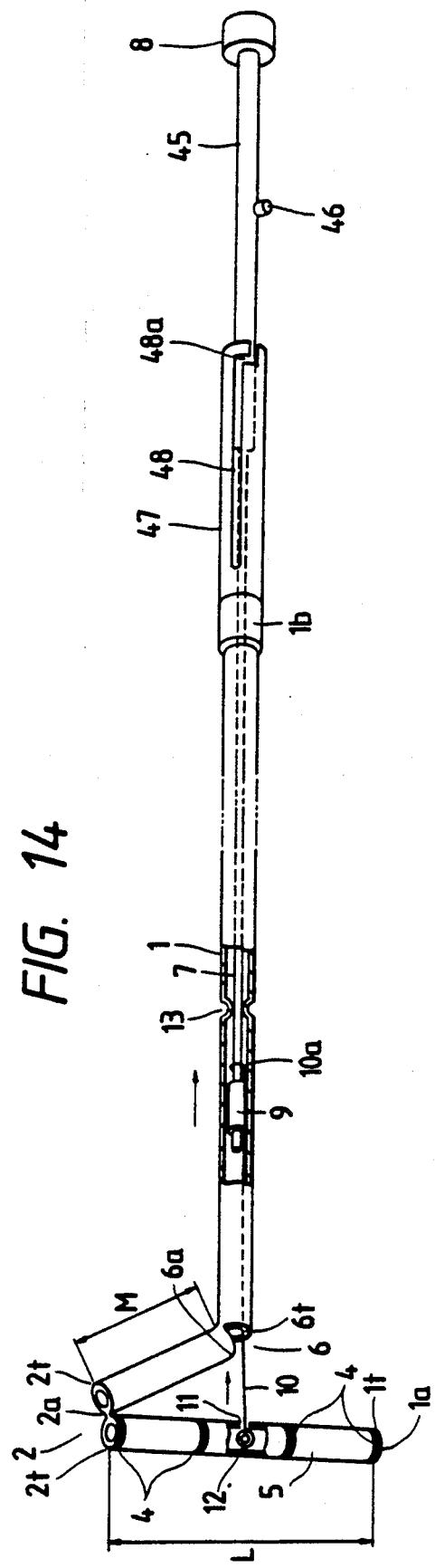
FIG. 13
FIG. 14

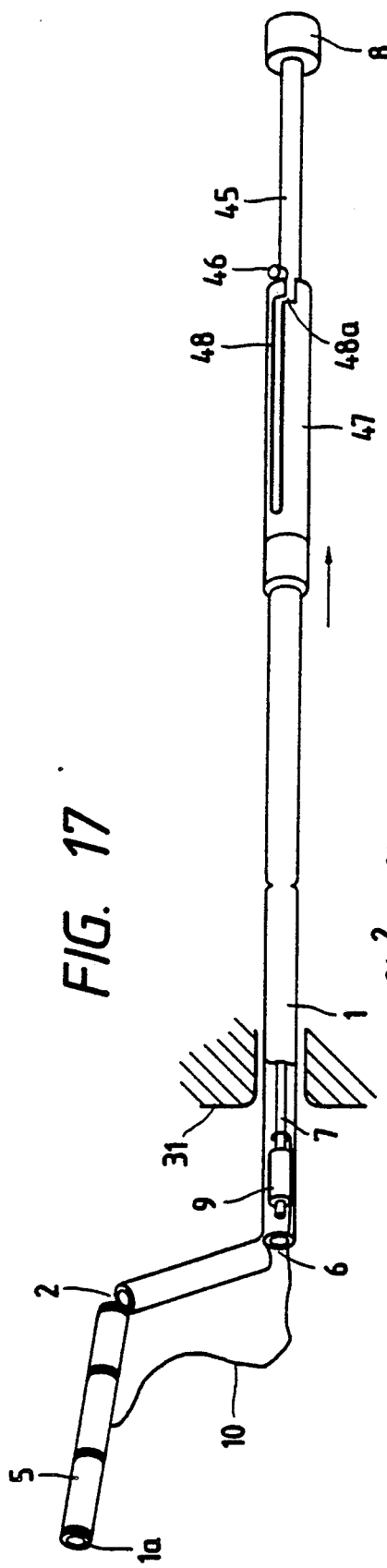
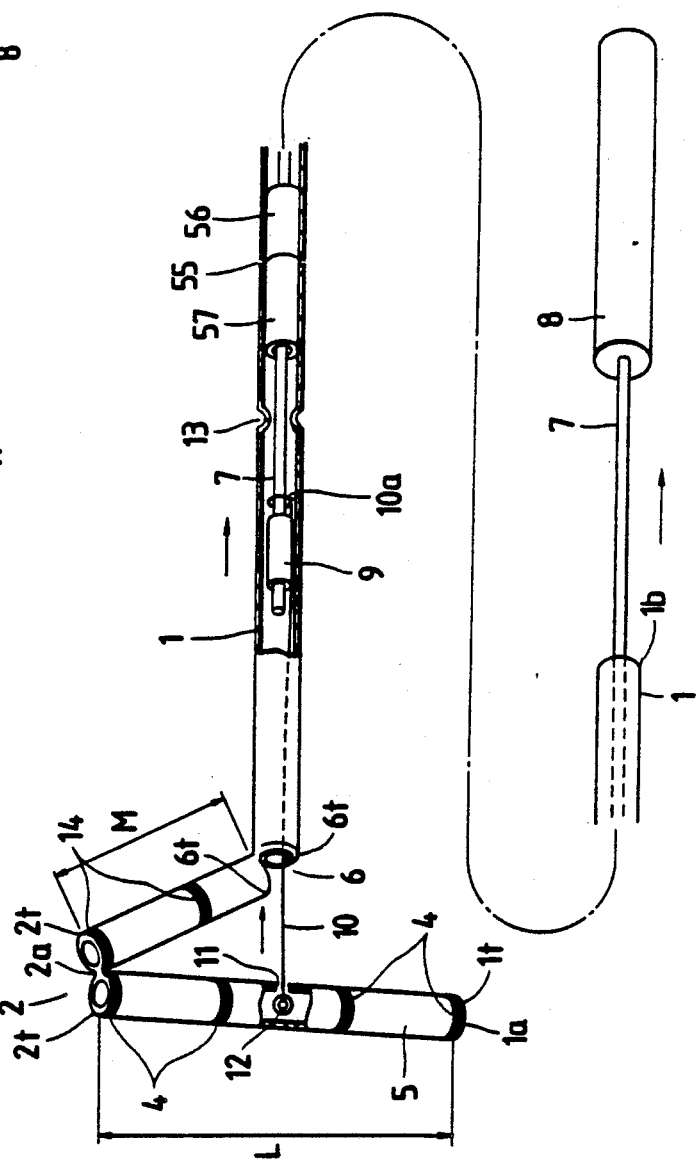
FIG. 17
FIG. 18

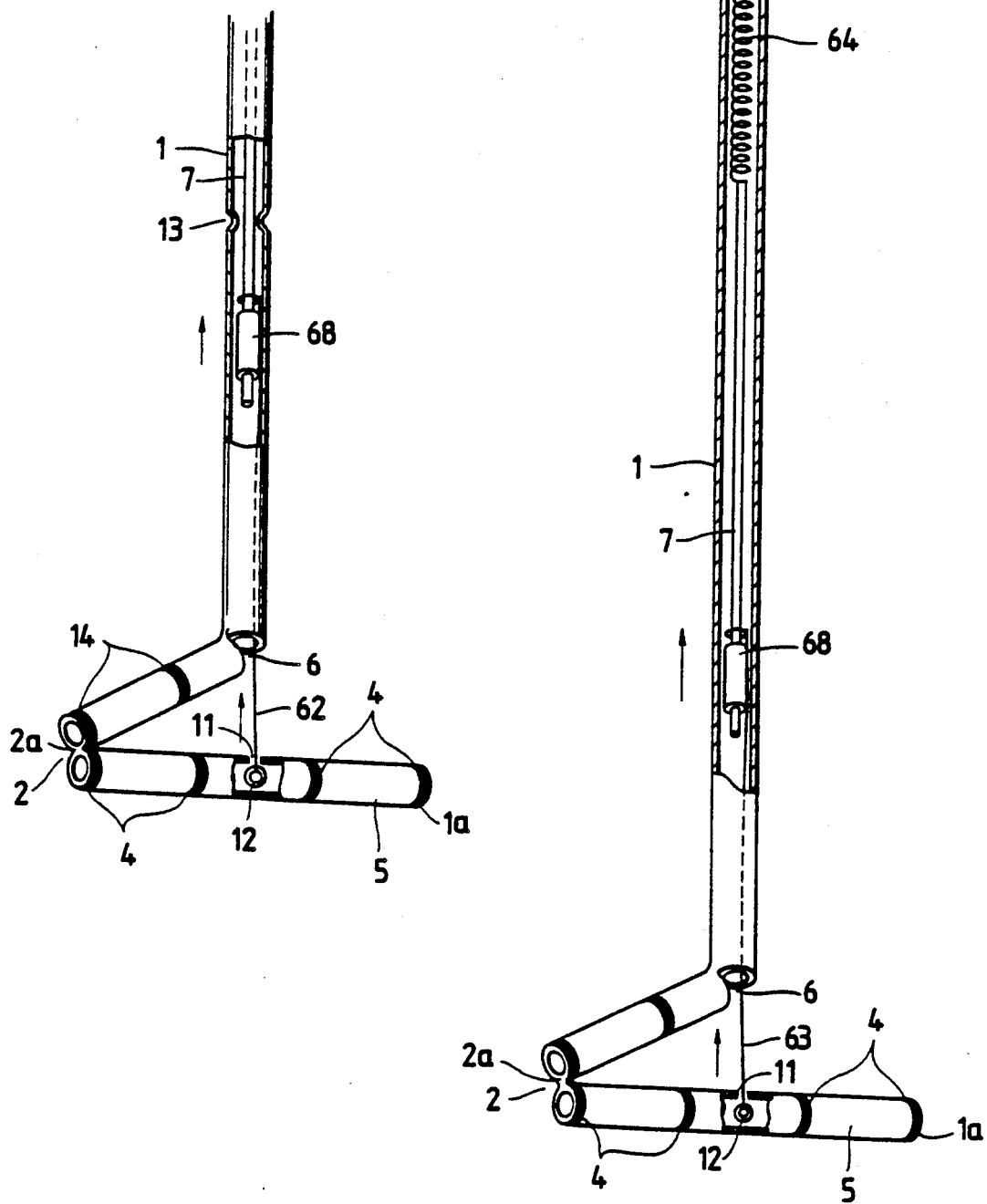

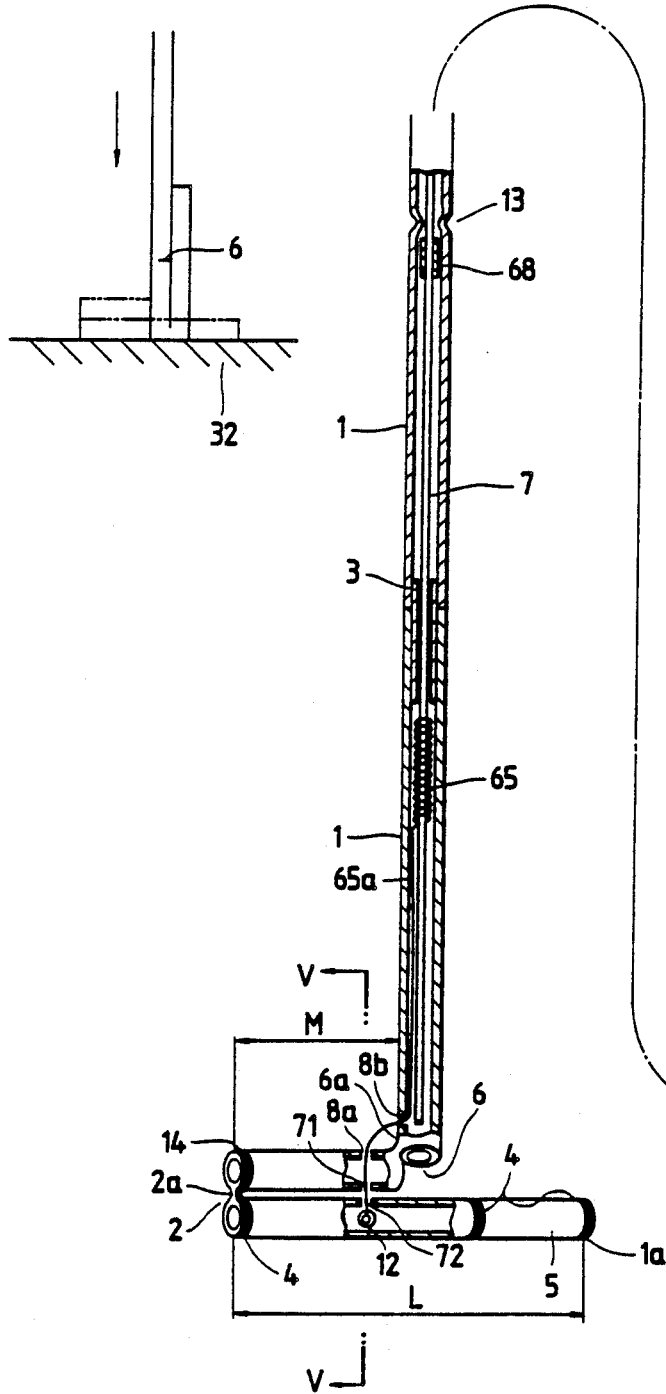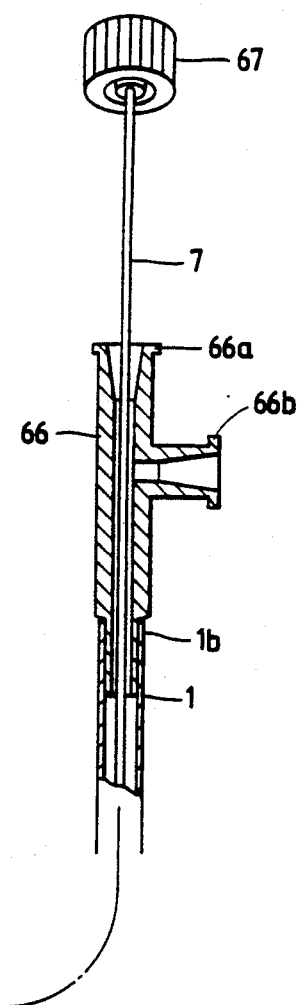
FIG. 27
FIG. 28

FIG. 38
FIG. 39
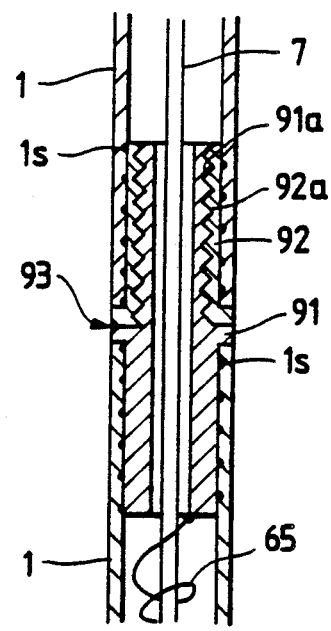
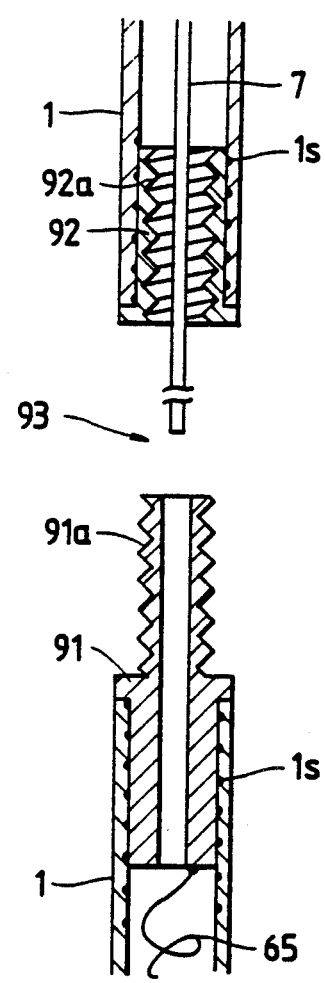

LENGTH-MEASURING DEVICE AND REFERENCE COLOR DISPLAY DEVICE FOR COLOR TONE ADJUSTMENT FOR USE IN COMBINATION WITH ENDOSCOPE

BACKGROUND OF THE INVENTION

This invention relates to a length-measuring device adapted to be inserted through a forceps channel in an endoscope so as to measure the size of the affected part in a body cavity of a patient, and also relates to a reference color display device for adjusting a color tone of an image picked up by the endoscope and displayed on a monitor of the endoscope.

One conventional length-measuring device of this general type for use with an endoscope comprises a scale member which has a scale and is bendable into an L-shape. Since the scale member can be projected only in one direction, such a conventional device can be used effectively only when the scale member is projected to a direction which allows an easy observation of the scale member in its field of vision. In addition, it is almost impossible to adjust the direction of projection of the scale member.

To overcome the above problem, there has been proposed a length-measuring device (as disclosed in Japanese Utility Model Publication No. 23441/87) in which an openable member, which can be opened or extended in opposite directions by a resilient force, is inserted into a flexible tube so as to be projected therefrom. The openable member comprises a pair of elongated elements between which a scale member, having scale marks spaced from one another at a predetermined interval, is connected. When the openable member is forced out of the flexible tube, the openable member is opened by its own resilient force, so that the scale member is extended uniformly on opposite sides of the axis of the flexible tube, thereby enabling an accurate length measurement of the affected part at the center of the field of vision of the endoscope.

In this conventional length-measuring device, however, the direction of extension of the scale member (i.e., its angle relative to the flexible tube) is predetermined, and therefore when the scale member 61 approaches the target affected part 62 in a direction oblique thereto as shown in FIG. 1, the size of the affected part can not be measured accurately. Moreover, the openable member must be so constructed that it can be positively opened in the opposite directions. When a measurement is to be effected, the openable member inserted into the flexible tube in its closed condition against its resilient force must be forced out of the flexible by a remote manipulation using an operating wire. Therefore, the operating wire is often buckled or suffers an improper operation. Thus, this conventional device can not always be handled easily. Further, since the overall construction must be firm, the manufacturing cost is increased and the device is too expensive for a scale.

Also, in conventional length-measuring devices, a flexible tube is of a unitary or integral construction from its proximal to distal end. If a length-measuring portion exceeds about 10 mm, it gets caught in the bronchus or other parts. In contrast, if the length-measuring portion is less than about 20 mm, a required measurement can not be carried out in the stomach and the colon. Therefore, the length-measuring portion has to be selected so that its length is in accordance with the part to be measured and with the intended purpose.

With the conventional length-measuring devices, however, since the flexible tube is of a unitary or integral construction from its proximal to distal end, a large set of length-measuring devices having the respective length-measuring portions of different lengths must be provided.

Among the parts of a length-measuring device for use with an endoscope, the length-measuring portion is most susceptible to damage. In the conventional length-measuring devices, even if only the length-measuring portion has been damaged, the whole of the length-measuring device must be replaced by a new one, since the flexible tube is of a unitary or integral construction from its proximal to distal end. Therefore, to avoid the interruption of measurement many length-measuring devices of the same kind must be provided.

Thus, conventionally, many length-measuring devices of the same kind as well as a large set of length-measuring devices of many kinds must be provided. This is undesirable because of increased costs.

Recently, there have been extensively used so-called electronic endoscopes equipped with a solid image pickup element for transmitting an observed image. In this type of endoscope, it is necessary to pre-adjust a color tone of the image displayed on a monitor, and conventionally such adjustment has been carried out using a color chart having three primary colors (i.e., red, green and blue) or a white color chart. More specifically, such a chart is placed on a desk, and this chart is displayed on the monitor through the endoscope, and the color of the image of the chart displayed on the monitor is compared with the color of the actual chart so as to adjust a color tone of the image displayed on the monitor.

However, the endoscope is used to observe the body cavity, and the reflection, scattering and absorption of the illumination light within the body cavity are different from those on the desk, resulting in the difference in the color reproduction of the object. As a result, even if the color tone adjustment is very strictly made on the desk, the object observed within the body cavity can not be accurately reproduced and therefore an accurate diagnosis of the affected part in the body cavity can not be made.

To overcome the above problem, it has been proposed to insert the endoscope into the body cavity so as to carry out a color tone adjustment using an image of the mucous membrane surface within the body cavity. With this method, however, there is no reference based on which the color tone adjustment is to be carried out objectively, and the color tone adjustment is made in accordance with the subject of the operator. Therefore, it is very difficult to accurately reproduce the color.

SUMMARY OF THE INVENTION

It is therefore an object of this invention to provide a length-measuring device for use with an endoscope, in which a scale can be always be brought into intimate contact with a target part at the center of the field of vision, and which device can be easily handled and can be manufactured at low cost.

Another object is to provide a length-measuring device for use with an endoscope which device can be smoothly inserted into and removed from the endoscope, is excellent in durability, and eliminates the risk of damaging the mucous membrane surface and other parts.

A further object is to provide a length-measuring device for use with an endoscope, in which a flexible tube can be easily and positively cleaned or sterilized.

A still further object is to provide a length-measuring device for use with an endoscope which device can be positively withdrawn from a forceps channel in the endoscope, thereby providing for a high degree of safety.

A further object is to provide a length-measuring device for use with an endoscope in which the orientation of a length-measuring portion can be varied freely with respect to the field of vision of the endoscope, thereby ensuring that an accurate measurement can always be carried out.

A further object is to provide a length-measuring device for use with an endoscope, in which a length-measuring portion can be easily brought into intimate contact with a target part even in a direction oblique thereto to thereby enable a measurement of the size of the target part at the center of the field of vision, and after the measurement, the device can be quickly withdrawn from a forceps channel in the endoscope.

A further object is to provide a length-measuring device for use with an endoscope, in which a length-measuring portion can be easily brought into intimate contact with a target part even in a direction oblique thereto to thereby enable a measurement of the size of the target part at the center of the field of vision, and the measuring operation can be done easily, and there is no risk of damaging the affected part and other parts.

A further object is to provide a length-measuring device for use with an endoscope, in which a length-measuring portion can be easily brought into intimate contact with a target part even in a direction oblique thereto to thereby enable a measurement of the size of the target part at the center of the field of vision, a distal end of a flexible tube can be positively folded into a T-shape, and a core rod is not kept projected from a slit in the tube.

A further object is to provide a length-measuring device for use with an endoscope, by which there is obviated the need for providing many kinds of length-measuring devices, thereby reducing the cost.

A further object is to provide a reference color display device for color tone adjustment for use with an endoscope, in which a proper color tone adjustment can be carried out to accurately reproduce, on a monitor, the color of an object observed within a body cavity.

According to a first aspect of the invention, there is provided a length-measuring device for use with an endoscope, comprising:

(a) a tube having a first slit formed therein and a second slit formed therein and disposed rearwardly of the first slit, said tube being bendable at each of the first and second slits, and said tube further having a length-measuring portion extending forwardly from the first slit to a distal end of said tube; and (b) means for bending said tube at the first and second slits.

The first and second slits formed or cut in the tube can be displaced from each other circumferentially of the tube. The bending means can comprise a pulling wire which has a connecting relation with the length-measuring portion to pull the same.

When the length-measuring device is to be inserted through a forceps channel in the endoscope, the tube is kept in a straight condition throughout its entire length. Then, when the pulling wire is pulled toward the proximal side, the tube is bent at the first slit, so that the length-measuring portion is turned 180 degrees (see FIG. 4). In this condition, when the tube is pressed against the target affected part, the tube is bent at the second slit, so that the length-measuring portion is brought into intimate contact with the affected part (see FIGS. 5 and 6). Since the tube can be bent at the first and second slits, the length-measuring portion can be brought into intimate contact with the affected part even in a direction oblique thereto.

A first through hole can be formed through the peripheral wall of the portion of the tube extending between the first and second slits, in which case a pair of second and third through holes are also formed through the peripheral wall of the length-measuring portion and disposed on opposite sides of the second slit. The pulling wire is introduced into the tube through the first through hole, and extends outwardly from the tube through the second through hole, and is again introduced into the tube through the third hole. The pulling wire has at its distal end a connecting relation with the length-measuring portion. With this arrangement, when the pulling wire is pulled, the tube is bent at the first and second slits in such a manner that the distal end portion of the tube is positively folded into a T-shape.

The edges in the outer peripheral surface of the tube at the first and second slits can be chamfered. In this case, these edges will not interfere with the internal parts of the endoscope when the length-measuring device is inserted into and removed from the forceps channel in the endoscope, thus ensuring smooth insertion and removal. In addition, when the length-measuring device is pressed against the wall of the body cavity, the chamfered edges will not damage the mucous membrane surface of the body cavity.

The bending means can also comprise a resilient member. This arrangement ensures very quick withdrawal of the length-measuring device from the forceps channel.

According to a second aspect of the invention, there is provided a length-measuring device for use with an endoscope, comprising:

(a) a tube having a first slit formed therein and a second slit formed therein and disposed rearwardly of the first slits, said tube being bendable at each of the first and second slit, and said tube further having a length-measuring portion extending forwardly from the first slit to a distal end of said tube;

(b) means for bending said tube at the first and second slits; and (c) a core rod inserted into said tube from a proximal end of said tube and extending to a position near the distal end of said tube, whereby when said core rod in said tube is passed past the first slit toward the distal end of said tube, said tube can not be bent at said first and second slits, and when the core rod is retracted past the second slit toward the proximal end of said tube, said tube can be bent at the first and second slits.

The operating core rod is inserted into the tube from the proximal end of the tube so as to be movable along the tube. The bending means can comprise a pulling wire for pulling the length-measuring portion, one end of the pulling wire being connected to the distal end of the operating core rod while the other end of the pulling wire has a connecting relation with the length-measuring portion. The operating core rod comprises, for example, a single optical fiber.

When the length-measuring device is to be inserted through a forceps channel in the endoscope, the tube is kept in a straight condition throughout its entire length. At this time, the distal end of the operating core rod is disposed between the first slit and the distal end of the tube, and therefore the tube is not bent at the first and second slits when it is inserted through the forceps channel. Then, the core rod is pulled in such a manner that its distal end is disposed rearwardly of the second slit, thus enabling the bending of the tube at the first and second slits. Then, the length-measuring portion is brought into intimate contact with the target affected part, as described above.

Since the core rod is inserted into the tube, the tube has such a degree of strength that the tube is hardly buckled. When a single optical fiber is used as the operating core rod, the core rod has a suitable degree of flexibility and strength and is easily released from its bent condition.

There can be provided means for limiting retracting movement of the core rod, which means may consist of a stopper mounted on a distal end portion of the core rod and a constricted portion of the tube.

There can also be provided stopping means for stopping the core rod in such a position that the distal end of the core rod is disposed rearwardly of the second slit. This facilitates the removal of the tube from the forceps channel in the endoscope.

The core rod can be normally urged in its retracting direction, that is, toward the proximal side of the device. With this arrangement, when the core rod is inadvertently pushed toward the distal end of the tube during the measuring operation, the core rod is immediately returned under the urging force.

According to a third aspect of the invention, there is provided a length-measuring device for use with an endoscope, comprising:

(a) a tube having a first slit formed therein and a second slit formed therein and disposed rearwardly of the first slit, said tube being bendable at each of the first and second slits, and said tube further having a length-measuring portion extending forwardly from the first slit to a distal end of said tube;

(b) means for bending said tube at the first and second slits; and (c) a liquid supply port provided at a proximal end portion of said tube for supplying a liquid such as a cleaning liquid into said tube.

When a cleaning liquid is applied into the tube from the liquid supply port, the cleaning liquid flows through the tube to the distal end of the tube to thereby drive foul matter, blood, etc. out of the tube. If an outer tube is mounted on the tube to cover the first and second slits, most of the cleaning liquid is discharged from the open distal end of the tube, thus cleaning the interior of the tube more effectively. Instead of the cleaning liquid, a sterilizing liquid can be used to sterilize the interior of the tube.

According to a fourth aspect of the invention, there is provided a length-measuring device for use with an endoscope, comprising:

(a) a tube having a first slit formed therein and a second slit formed therein and disposed rearwardly of the first slit, said tube being bendable at each of the first and second slits, and said tube further having a length-measuring portion extending forwardly from the first slit to a distal end of said tube;

(b) means for bending said tube at the first and second slits;

(c) a core rod inserted into said tube from a proximal end of said tube and extending to a position near the distal end of said tube, whereby when the core rod in said tube is passed past the first slit toward the distal end of said tube, said tube can not be bent at said first and second slits, and when the core rod is retracted past the second slit toward the proximal end of said tube, said tube can be bent at the first and second slits; and (d) a mouthpiece mounted on the proximal end of said tube and having a liquid supply port for supplying a liquid such as a cleaning liquid into said tube, said mouthpiece further having at its proximal end an opening through which said core rod is projected outwardly from the mouthpiece.

The interior of the tube can be cleaned by the cleaning liquid as described above, and the length-measuring portion can be brought into intimate contact with the affected part as described above. A manipulation thumbpiece can be mounted on the proximal end of the core rod, which is engageable with the opening of the tube in a water-proof manner.

According to a fifth aspect of the invention, there is provided a length-measuring device for use with an endoscope, comprising:

(a) a tube having a first slit formed therein and a second slit formed therein and disposed rearwardly of the first slit, said tube being bendable at each of the first and second slit, and said tube further having a length-measuring portion extending forwardly from the first slit to a distal end of said tube;

(b) means for bending said tube at the first and second slits; and (c) a cut portion being cut through at a position disposed rearwardly of the second slit to divide said tube into two parts, the two parts of said tube being connected together at the cut portion in such a manner that the two parts are rotatable about the axis of said tube.

With this construction, the tube is bent at the first and second slits by the bending means, and the length-measuring portion is pressed against the target affected part, so that the distal end portion of the tube assumes a T-shape. At this time, if the orientation of the length-measuring portion is not proper, the whole of the endoscope is rotated about its axis. As a result, the proximal part of the tube extending rearwardly of the cut portion is rotated in response to the rotation of the endoscope whereas the distal part of the tube extending forwardly of the cut portion is held stationary since the length-measuring portion is pressed against the affected part. Thus, the orientation of the length-measuring portion with respect to the field of vision of the endoscope can be suitably changed to achieve a good observation of the length-measuring portion.

According to a sixth aspect of the invention, there is provided a length-measuring device for use with an endoscope, comprising:

(a) a tube having a first slit formed therein and a second slit formed therein and disposed rearwardly of the first slit, said tube being bendable at each of the first and second slits, and said tube further having a length-measuring portion extending forwardly from the first slit to a distal end of said tube; and (b) means for bending said tube at the first and second slits; and (c) a divided portion being cut through at a position disposed rearwardly of said second slit to divide said tube into a proximal portion and a distal portion, the proximal and distal portions of said tube being releaseably connected together at the divided portion.

With this construction, a distal portion of the tube can be replaced by another distal portion having the length-measuring portion of the same length or a different length. Thus, a desired one of the distal end portions can be selectively used in accordance with the intended purpose.

According to a seventh aspect of the invention, there is provided a reference color display device for color adjustment for used with an endoscope, comprising:

a tube having a distal end portion which can be bent from a straight condition to a generally T-shaped condition by a remote manipulation from a proximal side of said tube, the distal end portion being colored in at least one reference color for adjusting a color tone of an image picked up by the endoscope and displayed on a monitor of the endoscope.

For using the reference color display device for color tone adjustment, the endoscope (electronic endoscope) is first inserted into the body cavity of the patient. The distal end portion of the tube is kept straight, and the tube is inserted through a forceps channel in the endoscope. When the distal end portion of the tube is extended from the endoscope, the distal end portion of the tube is bent or folded into a T-shape by a remote manipulation from the proximal side of the device. Then, when the distal end portion is pressed against the surface of the mucous membrane of the body cavity, the distal end portion having the reference color section lies substantially flush with the mucous membrane surface, and can be observed in the vicinity of the center of the field of vision of the endoscope. In this condition, the color tone of the image picked up by the endoscope and displayed on the monitor is adjusted. The distal end portion of the tube can be colored in a plurality of reference colors (for example three primary colors).

BRIEF DESCRIPTION OF THE DRAWINGS

FIG. 13 is a schematic view showing the length-measuring device of the first embodiment in its actual use;

FIG. 14 is a partly-broken perspective view of a length-measuring device according to a fifth embodiment of the invention;

FIG. 17 is a perspective view of the length-measuring device of the fifth embodiment showing the operation of withdrawing it from a forceps channel in the endoscope;

FIG. 18 is a view similar to FIG. 2, but showing a length-measuring device according to a sixth embodiment of the invention;

FIGS. 25 and 26 are partly-broken, fragmentary perspective views of length-measuring devices according to eighth and ninth embodiments of the invention, respectively;

FIG. 27 is a fragmentary side-elevational view of the length-measuring device of the first embodiment in its actual use;

FIG. 28 is a view similar to FIG. 2, but showing a length-measuring device according to a tenth embodiment of the invention:

FIG. 38 is an enlarged cross-sectional view of a portion of FIG. 36;

FIG. 39 is an enlarged cross-sectional view of a portion of FIG. 37;

DESCRIPTION OF THE PREFERRED EMBODIMENTS

The present invention will now be described with reference to the drawings.

Figure 1:
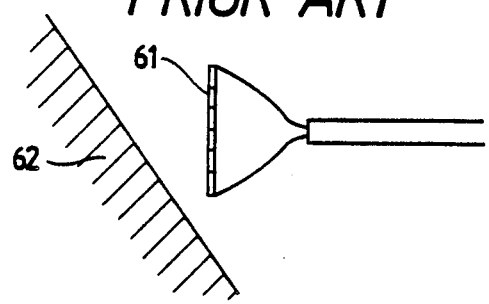
FIG. 1 is a fragmentary side-elevational view of a conventional length-measuring device for use with an endoscope.
Figure 2:
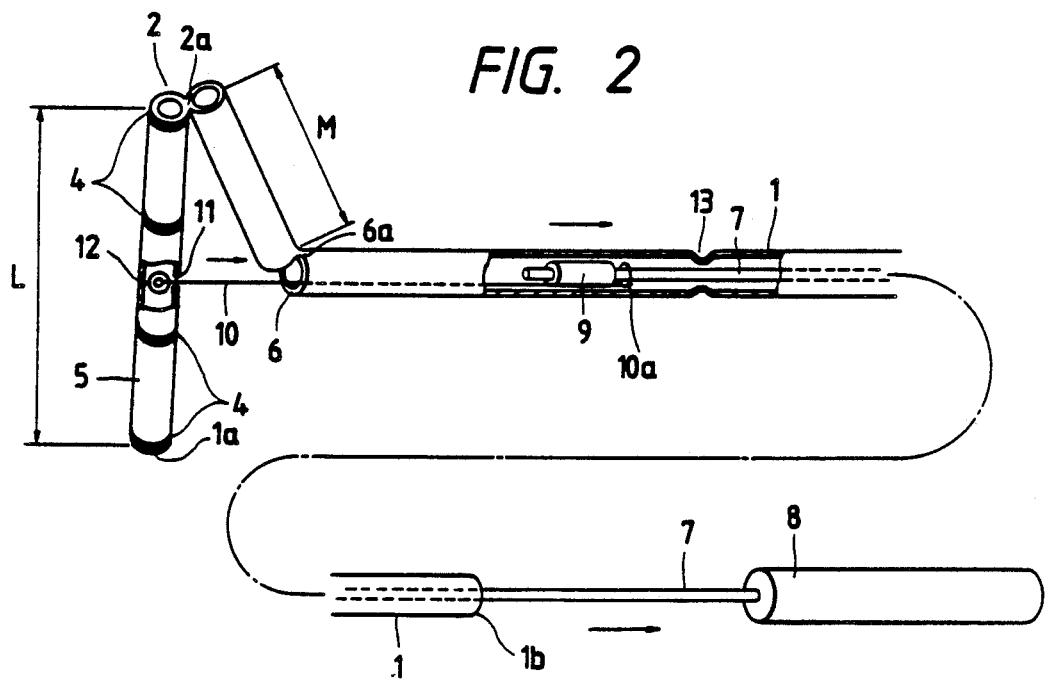
FIG. 2 is a partly-broken, perspective view of a length-measuring device for an endoscope according to a first embodiment of the invention.

FIG. 2 shows a length-measuring device for use with an endoscope, which is a first embodiment of the present invention. This device comprises a flexible tube 1 made, for example, of a tetrafluoroethylene resin, and the tube 1 has an outer diameter of about 1.5 mm to about 2.5 mm and a thickness of about 0.2 mm to about 0.5 mm. A first slit 2 is cut transversely in the tube 1 and is spaced a distance L from the distal end 1a of the tube 1, the slit 2 being cut in the tube 1 by a razor or the like. The distance L is, for example, about 10 mm to 50 mm, and can be set to a suitable value in this range to meet the intended purpose.

At the portion of the tube 1 where the first slit 2 is provided, the tube 1 is cut, with a slight connective section 2a remaining. The tube 1 can be freely bent at this portion like an articulation.

Scale marks 4 are provided on the distal end portion of the tube 1 disposed forwardly of the first slit 2, and this portion 5 serves as a length-measuring portion for measuring the size of the affected part or other parts. Each scale mark 4 is, for example, a line of coating applied circumferentially to the outer peripheral surface of the tube 1. For example, the scale marks 4 are applied to the tube 1 in a manner to divide the portion 5 into three sections. The intervals of the scale marks 4 can be greater or smaller depending on the intended purposes, and also may be of different colors.

A second slit 6 is cut transversely in the tube 1 and is spaced a distance M from the first slit 2 toward the proximal end of the tube 1. Therefore, the tube 1 can also be freely bent at this portion. It will suffice that the distance M is shorter than the length of the length-measuring portion 5, and it is most preferred that the distance M is about a half of the distance L. In this embodiment, the second slit 6 is cut from a direction 180 degrees displaced circumferentially from the first slit 2.

An operating core rod 7 is inserted into the tube 1 from the proximal end 1b of the tube 1 so as to be movable toward and away from the distal end of the tube 1, the core rod 7 being generally equal in length to the tube 1. Although the operating core rod 7 may be a stainless steel wire or a coil, it is preferred that the core rod 7 be a single optical fiber having a diameter of about 0.2 mm to 1 mm because such a fiber has a suitable degree of flexibility and strength and is easily released from its bent condition. The above single optical fiber corresponds to one of plural fibers constituting a commonly used optical fiber bundle. In this embodiment, as the core rod 7, there is used a single optical fiber sheathed by a synthetic resin tube having a thickness of about 0.1 mm.

The operating core rod 7 extends outwardly from the proximal end of the tube 1, and a manipulation thumbpiece 8 is attached to this extended portion of the core rod 7. A stopper 9, for example in the form of a metal tube, is fixedly mounted on the distal end of the operating core rod 7 by an adhesive or by pressing. A pulling wire 10, for example in the form of a silkworm gut (fishing gut) which is thin and flexible and has a diameter of about 0.03 mm to 0.2 mm, is tied at one end to the portion of the operating core rod 7 disposed adjacent to and rearwardly of the stopper 9. In this embodiment, the one end of the pulling wire 10 is formed into a loop through which the operating core rod 7 is loosely passed. Thus, the pulling wire 10 is not tightly tied to the core rod 7.

With this arrangement, when the operating core rod 7 is pulled toward the proximal end, the tied portion 10a of the pulling wire 10 is engaged with the stopper 9, so that the pulling wire 10 is also pulled in the same direction. Alternatively, the pulling wire 10 may be passed through the tube 1 toward the proximal end of the tube 1 so that the pulling wire 10 can be directly pulled from the proximal end.

The pulling wire 10 extends exteriorly from the tube 1 through the second slit 6. The distal end of the pulling wire 10 passes through a through hole 11, formed in the central portion of the length-measuring portion 5 of the tube 1 and is tied to a retainer ring 12 disposed within the length-measuring portion 5. Therefore, when the manipulation thumbpiece 8 is pulled at the proximal end, the pulling wire 10 is pulled through the operating core rod 7, and accordingly the length-measuring portion 5 of the tube 1 is pulled toward the second slit 6 by the pulling wire 10, so that the first and second slits 2 and 6 are gradually bent. Then, when the length-measuring portion 5 is bent or turned 180 degrees, the rear end of the stopper 9 is brought into engagement with a constricted portion 13 of the tube 1, thereby preventing further pulling of the operating core rod 7.

Figure 3:
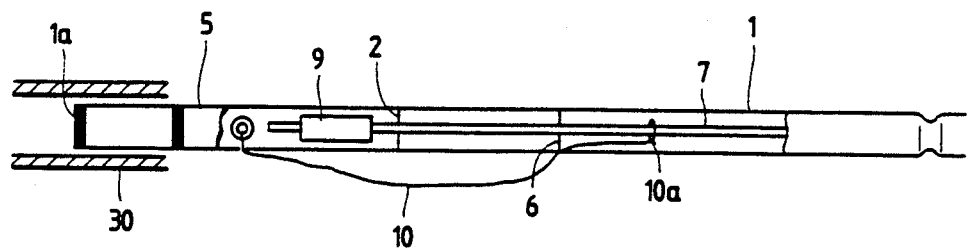
FIGS. 3 to 5 are side-elevational views showing the operation of the length-measuring device of the first embodiment.
Figure 4:
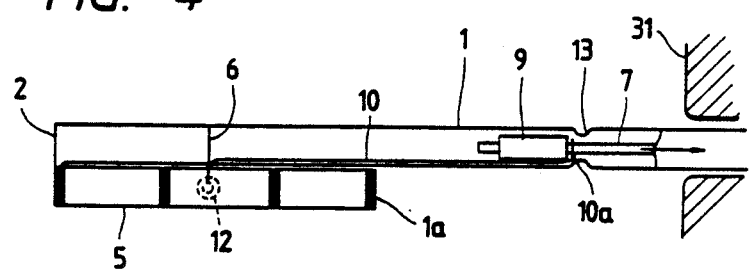
Figure 5:
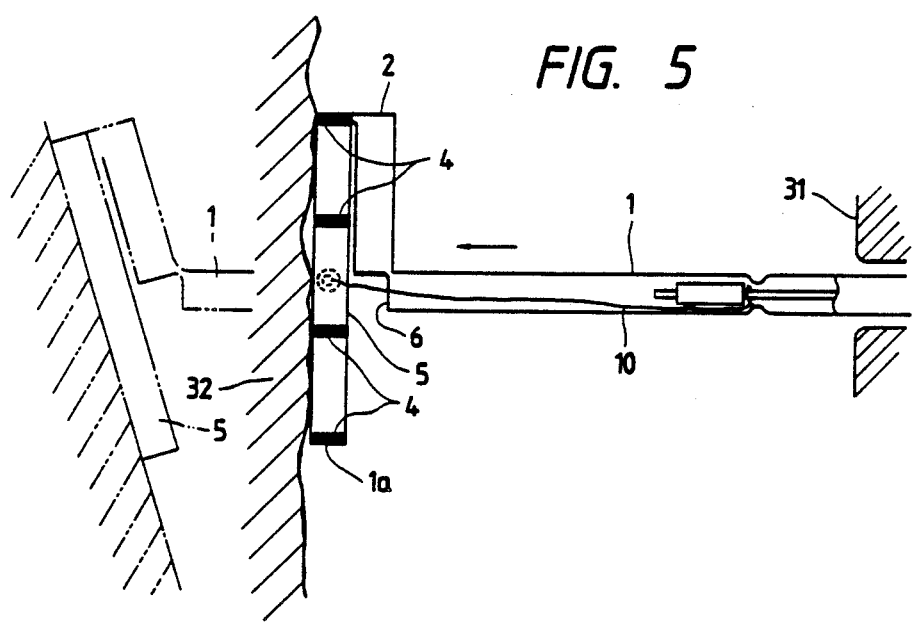

FIGS. 3 to 5 show a sequence of the operation of the length-measuring device for an endoscope in the above embodiment. In these figures, the wall of the tube 1 is schematically indicated by solid lines for illustration purposes.

First, as shown in FIG. 3, the operating core rod 7 is inserted into the tube 1 to such an extent that its distal end portion is disposed within the length-measuring portion 5. In this condition, since the operating core rod 7 is passed past the first and second slits 2 and 6, the tube 1 can not be bent or folded at the first and second slits 2 and 6. Therefore, the length-measuring device in this condition can be easily inserted through a forceps channel 30 of the endoscope.

When the distal end of the length-measuring device for the endoscope is projected from the distal end 31 of the endoscope, the manipulation thumbpiece 8 is pulled rearwardly until the stopper 9 is brought into engagement with the constricted portion 13. As a result, as shown in FIG. 4, the length-measuring portion 5 is bent or turned 180 degrees at the first slit 2 and is directed rearwardly.

Then, the distal end of the thus bent tube 1 in its condition shown in FIG. 4 is brought into engagement with the affected part (i.e., the target part) of the patient, the tube 1 is bent or turned at the second slit 6, so that the distal end portion of the tube 1 assumes a T-shape as shown in FIG. 5. Therefore, the length-measuring portion 5 is always disposed at the center of the field of vision of the endoscope, and therefore the size of the affected part can be read by the scale marks 4. Even when the tube 1 approaches the affected part in oblique relation thereto, the length-measuring portion 5 can be bent at the second slit 6 into intimate contact with the affected part merely by pressing the distal end of the tube 1 against the affected part, as shown in phantom in FIG. 5. Therefore, even when the tube 1 approaches the affected part in any direction oblique to the affected part, the length-measuring portion 5 can be brought into intimate contact with the affected part, thereby enabling an easy measurement at the center of the filed of vision.

Figure 6:
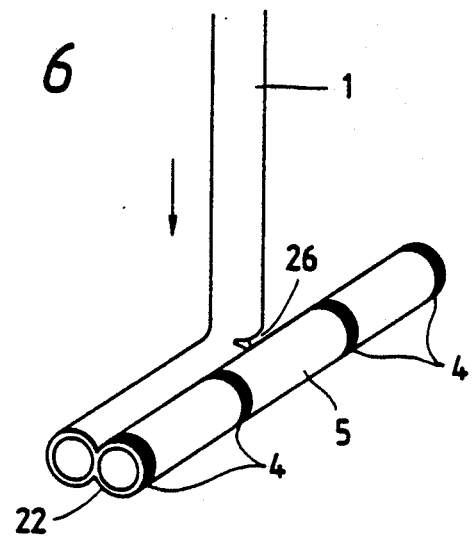
FIG. 6 is a fragmentary perspective view of a length-measuring device according to a second embodiment of the invention.

FIG. 6 shows a length-measuring device of a second embodiment of the invention in its operative condition. In this embodiment, a first slit 22 and a second slit 26 formed or cut in the tube 1 are circumferentially displaced 90 degrees from each other. With this arrangement, the length-measuring portion 5 can be bent into juxtaposed relation to the tube 1, and therefore the scale can be more easily viewed.

In actual use, even in the first embodiment in which the first and second slits 2 and 6 are circumferentially displaced 180 degrees from each other, when the tube 1 is pressed against the affected part under a slightly increased force, the connective section 6a interrupting the second slit 6 is twisted, so that the length-measuring portion 5 is disposed in juxtaposed relation to the tube 1 as in FIG. 6. Therefore, practically, the first and second slits can be provided at any position in the circumferential direction of the tube 1 although it is preferred that the first and second slits be circumferentially displaced from each other.

The length-measuring devices for an endoscope according to the first and second embodiments can be easily removed from the forceps channel of the endoscope. After use, merely by withdrawing the tube 1 from the forceps channel, the bent distal end portion of the tube 1 is returned by itself to its initial straight condition along the forceps channel, so that the tube is removed from the forceps channel. Therefore, after use, there is not required any special operation for returning the length-measuring portion 5 into its initial condition.

In the length-measuring devices of the first and second embodiments, even when the tube approaches the target affected part in a direction oblique thereto, the length-measuring portion can be easily brought into intimate contact with the affected part, and the size of the affected part can be measured at the center of the field of vision. In addition, simple operations are only needed when using and removing the length-measuring device, and the device can be made only by a combination of the tubes and the wires, and therefore can be manufactured at low cost.

Although in the above embodiments the tube 1 is described as a the flexible tube, it is noted that the tube 1 is not always required to be flexible.

Figure 7:
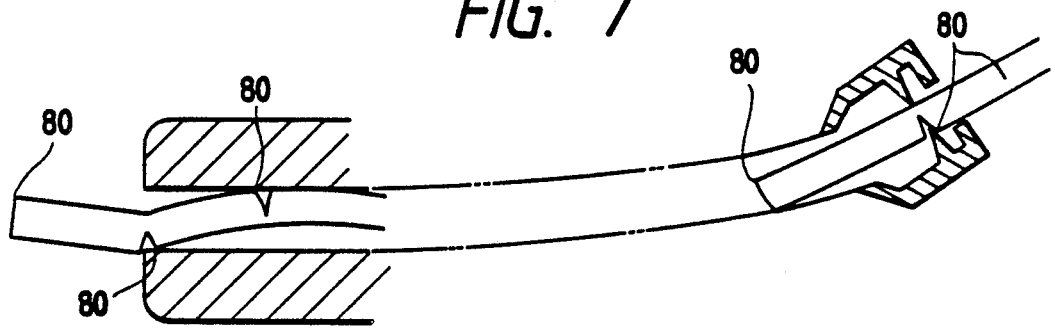
FIGS. 7 and 8 are fragmentary schematic views showing the length-measuring device of the first embodiment in its actual use.
Figure 8:
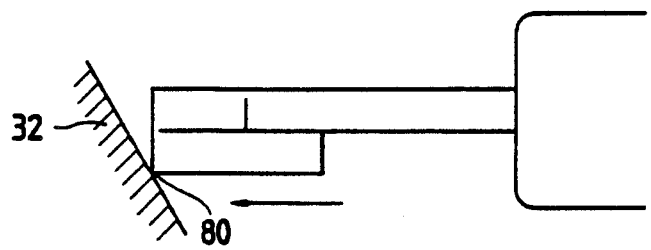

When the length-measuring device for an endoscope according to the first embodiment is inserted into and removed from the forceps channel, the distal end of the tube and the edges 80 of the slits may get caught on the inner parts of the endoscope as shown in FIG. 7, so that the insertion and removal of the tube can not be sometimes carried out smoothly. Thus, the operability is not entirely satisfactory, and the length-measuring device may be damaged by several times of its use.

Further, during the measuring operation, the edge 80 of the slit pressed against a wall 32 of the body cavity may damage the surface of the mucous membrane of the body cavity to cause bleeding or to create a cause of an ulcer.

A length-measuring device for an endoscope according to a third embodiment of the invention can be smoothly inserted into and removed from the endoscope, is excellent in durability, and eliminates the risk of damaging a surface of a mucous membrane of the body cavity.

Figure 9:
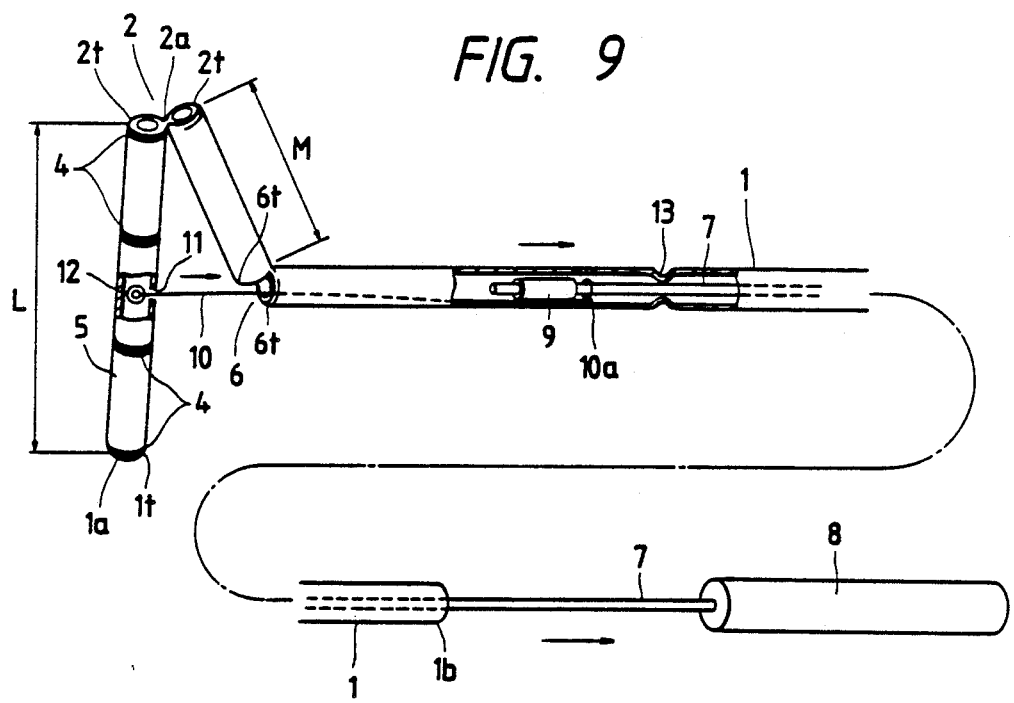
FIG. 9 is a view similar to FIG. 2, but showing a length-measuring device according to a third embodiment of the invention.
Figure 10:
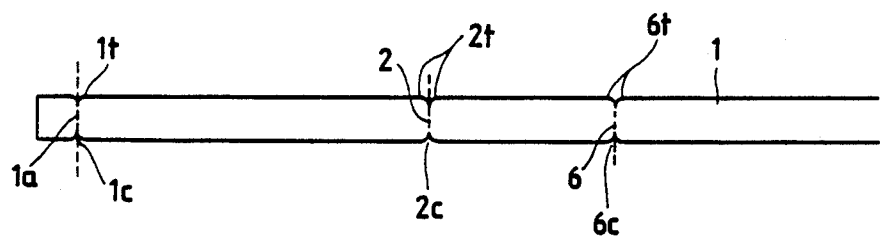
FIG. 10 is a side-elevational view of a tube material for explaining the processes to be exerted thereon.

The third embodiment shown in FIG. 9 differs from the first embodiment in the following points:

The outer edges of the distal end 1a of the tube 1, the first slit 2 and the second slit 6 are formed respectively into chamfered surfaces 1t, 2t and 6t which are smooth and rounded. Alternatively, these outer edges may be tapered. The chamfered surfaces 1t, 2t and 6t can be formed by heating. FIG. 10 shows the formation of these chamfered surfaces. First, constricted portions 1c, 2c and 6c are thermoformed on the tube 1 at those portions where the distal end 1a and the slits 2 and 6 are to be provided. Then, the constricted portion 1c is cut through at a median plane thereof, and the constricted portions 2c and 6c are suitably cut to form the slits 2 and 6 by a razor or the like.

As a result, the outer edges of the distal end 1a and the slits 2 and 6 are made to have the smooth chamfered surfaces 1t, 2t and 6t, respectively, and therefore these portions can be smoothly inserted into and removed from the forceps channel 30 and will not get caught by the inner surfaces of the endoscope.

When the length-measuring device is pressed against the affected part 32, the surface of the mucous membrane will not be damaged since the outer edges of the distal end 1a and the first and second slits 2 and 6 are all formed into the smooth chamfered surfaces 1t, 2t and 6t.

The length-measuring device for an endoscope according to the third embodiment can be easily removed from the forceps channel of the endoscope. Since the outer edges of the distal end 1a and the slits 2 and 6 are all chamfered, after use, merely by withdrawing the tube 1 from the forceps channel, the bent distal end portion of the tube 1 is returned by itself to its initial straight condition along the forceps channel so as not to interfere with the inner parts of the endoscope, so that the tube is removed from the forceps channel. Therefore, after use, there is not required any special operation for returning the length-measuring portion 5 into its initial condition.

As a modified form of the third embodiment, the first slit 2 and the second slit 6 may be arranged in the same manner as described above for the second embodiment (FIG. 6).

In the length-measuring devices of the third embodiment, even when the tube approaches the target affected part in a direction oblique thereto, the length-measuring portion can be easily brought into intimate contact with the affected part, and the size of the affected part can be measured at the center of the field of vision. In addition, simple operations are only needed when using and removing the length-measuring device, and the device can be made only by a combination of the tubes and the wires, and therefore can be manufactured at low costs. Further, since the length-measuring device can be smoothly inserted into and removed from the forceps channel of the endoscope, the device is excellent in operability and durability, and is also excellent from the viewpoint of safety since it eliminates the risk of damaging the surface of a mucous membrane of the body cavity.

In the length-measuring device for an endoscope according to the first embodiment, when the distal end of the tube is clogged with blood or foul matter, it is impossible to clean the interior of the tube by washing away the blood or foul matter. Therefore, the length-measuring device must be disposed of once it is used, otherwise one patient may infect another with the disease. Also, it is difficult to sterilize the interior of the tube before use, and therefore this may be sometimes undesirable from a sanitary point of view.

A length-measuring device for an endoscope according to a fourth embodiment of the invention overcomes such problems, and is of such a construction that the interior of the tube can be easily and positively cleaned (washed) and sterilized.

Figure 11:
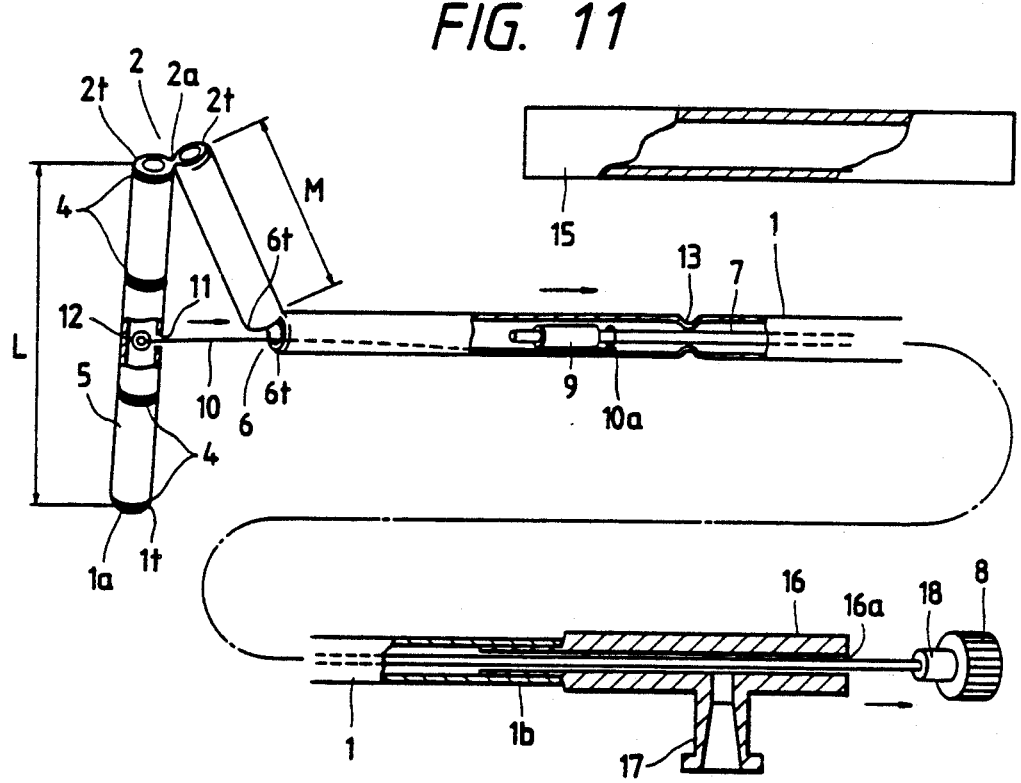
FIG. 11 is a view similar to FIG. 2, but showing a length-measuring device according to a fourth embodiment of the invention.

The fourth embodiment shown in FIG. 11 is based on the third embodiment (FIG. 9) and differs therefrom in the following points:

A mouthpiece 16 of a synthetic resin or metal is fixedly secured to a proximal end 1b of the tube 1 in such a manner that a bore of the mouthpiece 16 communicates with the bore or interior of the tube 1. The mouthpiece 16 has a liquid supply port 17 projecting outwardly from the side surface thereof and communicating with the interior of the tube 1 via the bore of the mouthpiece 16. In this embodiment, the liquid supply port 17 is in the form of a so-called Luer lock fitting, and a syringe (not shown) or the like is adapted to be connected to such a fitting so as to inject a cleaning liquid or the like into the tube 1. The liquid supply port 17 may take any other form than such a Luer lock fitting.

The proximal end portion of the operating core rod 7 passes through the mouthpiece 16 and projects outwardly from the proximal end of the mouthpiece 16. A manipulation thumbpiece 8 is fixedly secured to the proximal end of the operating core rod 7. A plug 18 formed integrally with the thumbpiece 8 can be fitted in an end opening 16a of the mouthpiece 16 to close the same. Therefore, when it is desired to supply a liquid from the liquid supply port 17, the opening 16a is closed by the plug 18, thereby preventing leakage of the liquid through the opening 16a.

Figure 12:
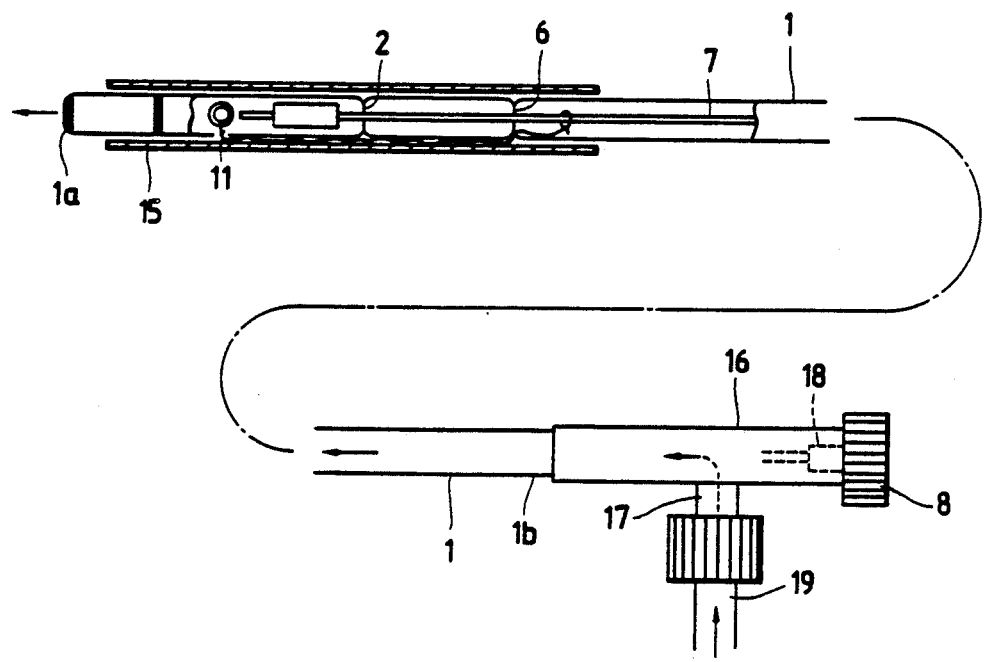
FIG. 12 is a side-elevational view of the length-measuring device of the fourth embodiment showing a cleaning operation.

In the fourth embodiment, an outer cover tube 15 is removably fitted on the distal end portion of the tube 1 to cover the first slit 2 and the second slit 6. The outer cover tube 15 is flexible and has such an inner diameter that the outer cover tube 15 is loosely fitted on the tube 1. When the length-measuring device is to be used, the outer cover tube 15 may be removed from the tube 1, as shown in FIG. 11, or alternatively the outer cover tube 15 may be slid along the tube 1 toward the proximal end 1b of the tube 1. The outer cover tube 15 can be held on the distal end portion of the tube 1 as shown in FIG. 12 when the length-measuring device is not in use and therefore is to be stored. Thus, in this case, the outer cover tube 15 serves as a protective cap for protecting the distal end portion of the length-measuring device against damage.

FIG. 12 shows a cleaning operation for washing away foul matter or blood adhering to the inner surface of the tube 1, after the length-measuring device is used.

As shown in FIG. 12, first the plug 18 formed integrally with the manipulation thumbpiece 8 is fitted in the opening 16a of the mouthpiece 16 to close the same. The outer cover tube 15 is fitted on the distal end portion of the tube 1 to cover the two slits 2 and 6 and the through hole 11. Then, a liquid supply device 19 such as a syringe is attached to the liquid supply port 17 to inject a cleaning liquid into the mouthpiece 16. As a result, the cleaning liquid flows through the mouthpiece 16 and the tube 1 and reaches the distal end portion of the tube 1 as indicated by arrows in FIG. 12.

Since the slits 2 and 6 and the through hole 11 are covered by the outer cover tube 15, most of the cleaning liquid is discharged under pressure from the open distal end 1a of the tube 1, thereby washing the foul matter or the blood out of the tube 1.

Also, by injecting a sterilization liquid in a similar manner before the length-measuring device is used, the interior of the tube 1 is sterilized.

As a modified form of the fourth embodiment, the first slit 2 and the second slit 6 can be arranged as described above for the second embodiment (FIG. 6).

In the length-measuring device for an endoscope according to the fourth embodiment, even when the tube approaches the target affected part in a direction oblique thereto, the length-measuring portion can be easily brought into intimate contact with the affected part, and the size of the affected part can be measured at the center of the field of vision. In addition, simple operations are only needed when using and removing the length-measuring device, and the device can be made only by a combination of the tubes and the wires, and therefore can be manufactured at low cost. Further, when the tube is clogged with foreign matter such as foul matters and the blood, such foreign matter can be easily washed away. This eliminates the risk of the transmission of a disease from one patient to another, and thereby the length-measuring device can be used repeatedly. The interior of the tube can be sterilized beforehand. Further, when the length-measuring device is not in use, the outer cover tube can be used as a protective cap for preventing damage to the length-measuring device.

The length-measuring device for an endoscope according to the first embodiment is not provided with means for limiting the forward and rearward movements of the operating core rod 7 in its halfway position. When the length-measuring device is to be withdrawn from the forceps channel 30 after the device is used, the operating core rod 7 is pushed toward the distal end of the tube 1 in order to loosen the pulling wire 10. At this time, the distal end 7a of the operating core rod 7 is often projected outwardly from the tube 1 through the second slit 6 as shown in FIG. 13, because of lack of the above limiting means. As a result, when the length-measuring device is pulled in a direction of an arrow in an attempt to withdraw it from the forceps channel 30, the length-measuring device becomes engaged with the end opening of the forceps channel 30, which not only disables the withdrawal of the length-measuring device but also damages or breaks the length-measuring device, so that there may be a risk of injuring the inner wall of the body cavity of the patient by a broken piece.

A length-measuring device for an endoscope according a fifth embodiment of the invention overcomes such problems and is so constructed as to be positively withdrawn from the forceps channel to provide a high degree of safety.

The fifth embodiment shown in FIG. 14 is based on the third embodiment (FIG. 9) and differs therefrom in the following points:

An operating rod 45 is connected to the proximal end of the operating core rod 7. The rod 45 is disposed outwardly of the tube 1, and the manipulation thumbpiece 8 is secured to the proximal end of the rod 45.

A guide pin 46 is formed on the outer surface of the rod 45 between the opposite ends of the rod 45. A guide tube 47 is connected to the proximal end of the tube 1 and communicates therewith. A guide slot 48 is formed in a peripheral wall of the guide tube 47 along the axis of the guide tube 47. The guide slot 48 is turned or bent in a crank-shaped manner in the vicinity of the proximal end of the guide tube 47. Reference numeral 48a denotes this crank portion.

Figure 15:
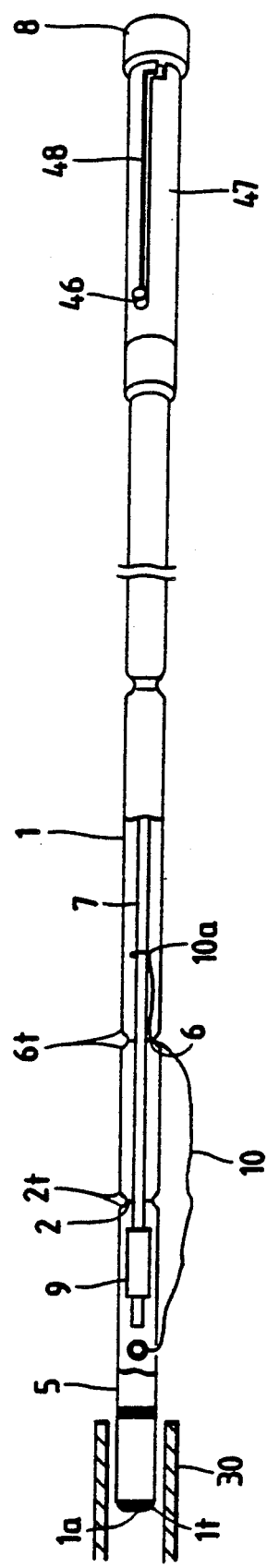
FIGS. 15 and 16 are side-elevational views showing the operation of the length-measuring device of the fifth embodiment.
Figure 16:
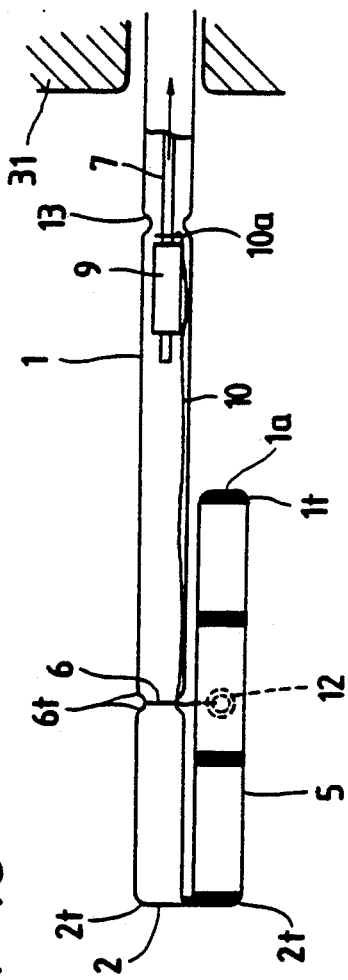

The guide slot 48 opens to the proximal end of the guide tube 47, and the guide pin 46 can be introduced into the guide slot 48 from this open end so as to be slidable along the guide slot 48. When the guide pin 46 is slidingly moved to the distal end of the guide slot 48, the distal end of the operating core rod 7 is inserted to a position between the distal end 1a of the tube 1 and the first slit 2 as shown in FIG. 15. On the other hand, when the operating core rod 7 is pulled to its outermost position (in a right-hand direction in the drawings) so that the guide pin 46 comes out of the guide slot 48, the rod 45 is retracted until the stopper 9, which comprises a metal pipe secured to the distal end of the operating core rod 7, is brought into engagement with the constricted portion 13 of the tube 1 as shown in FIG. 16. Thus, the opposite ends of the stroke of movement of the operating core rod 7 are defined in this manner.

When the rod 45 is pushed from its retracted condition toward the guide tube 47, the guide pin 46 abuts against either the proximal end of the guide tube 47 (see FIG. 17) or the crank portion 48a of the guide slot 48, whereupon the rod 45 is stopped. At this time, the distal end of the operating core rod 7 is disposed adjacent to and rearwardly of the second slit 6. Thus, the guide pin 46 and the guide slot 48 constitute means for stopping the distal end of the operating core rod 7 in the position adjacent to and rearwardly of the second slit 6. Also, in this condition, the pulling wire 10 is sufficiently fed outwardly of the tube 1 that the tube 1 can be straightened at the slits 2 and 6.

FIG. 17 shows the condition in which the length-measuring device for an endoscope according to the fifth embodiment is to be withdrawn from the forceps channel of the endoscope. At this time, when the rod 45 is pushed toward the guide tube 47, the guide pin 46 is brought into abutting engagement with either the proximal end of the guide tube 47 (see FIG. 17) or the crank portion 48a of the guide slot 48, whereupon the rod 45 is stopped. At this time, the distal end of the operating core rod 7 is disposed adjacent to and rearwardly of the second slot 6, and the pulling wire 10 is sufficiently fed outwardly of the tube 1 that the distal end portion of the tube 1 can be straightened.

Therefore, in this condition, merely by withdrawing the tube 1 from the forceps channel, the bent distal end portion of the tube 1 is returned into a straight condition by itself along the forceps channel without interfering with (or becoming engaged with) the inner parts of the endoscope.

As a modified form of the fifth embodiment, the first slit 2 and the second slit 6 can be arranged in the manner as described above for the second embodiment (FIG. 6).

In the length-measuring device for an endoscope according to the fifth embodiment, even when the tube approaches the target affected part in a direction oblique thereto, the length-measuring portion can be easily brought into intimate contact with the affected part, and the size of the affected part can be measured at the center of the field of vision. In addition, when the length-measuring device is to be withdrawn from the forceps channel, the distal end of the operating core rod can be stopped at the position near and rearwardly of the second slit, and therefore the bent portion of the tube is returned into a straight condition by itself along the forceps channel, thereby ensuring a positive withdrawal of the length-measuring device, which prevents damage to the length-measuring device and injury to the patient.

Even with the length-measuring device for an endoscope according to the first embodiment, the situation can occur that the scale marks on the length-measuring portion are not clearly recognized, depending on the orientation of the T-shaped length-measuring portion disposed in the field of vision. In such a case, it is quite difficult to rotate the length-measuring device about its axis within the forceps channel, and therefore the orientation of the length-measuring portion can not be changed with respect to the field of vision, thus failing to accurately measure the size of the affected part in the body cavity.

A length-measuring device according to a sixth embodiment of the invention overcomes such problems and is of such a construction that the orientation of the length-measuring portion can be freely changed with respect to the field of vision in order to always achieve an accurate measurement.

The sixth embodiment shown in FIG. 18 is based on the third embodiment (FIG. 9) and differs therefrom on the following points:

Scale marks 14, corresponding to the scale marks 4 on the length-measuring portion, are also formed on the outer peripheral surface of that portion of the tube 1 extending between the first slit 2 and the second slit 6.

Figure 19:
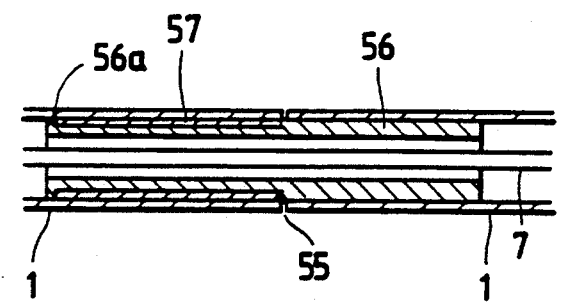
FIG. 19 is an enlarged cross-sectional view showing a portion in the vicinity of a cut portion of a flexible tube of the sixth embodiment.

The tube 1 is cut transversely therethrough at its portion located adjacent to and rearwardly of the constricted portion 13. Reference numeral 55 denotes this cut portion. As shown in FIG. 19, connecting pipes 56 and 57 are respectively fitted in and fixedly secured to those portions of the tube 1 located immediately adjacent to the cut portion 55 on the opposite sides of the cut portion 55. The connecting pipe 56 is rotatably fitted in the connecting pipe 57. One end 56a of the inner connecting pipe 56 is deformed into a greater diameter by pressing, so that the two connecting pipes 56 and 57 are connected together in a manner to prevent the two connecting pipes from becoming disengaged from each other. Thus, the two parts of the tube 1 separated from each other by the cut portion 55 are connected together at the cut portion 55 by the connecting pipes 56 and 57 so as to be rotatable about the axis of the tube 1.

In this embodiment, although the cut portion 55 is provided at the position disposed near and rearwardly of the constricted portion 13, the invention is not restricted to such arrangement, and it will suffice that the cut portion 55 is disposed relatively near to the length-measuring portion 5 and rearwardly of the second slit 6. However, in the case where the stopper 9 is slidable within the tube 1 as in this embodiment, it is preferred that the cut portion 55 be provided at those portions other than a sliding range.

Figure 20:
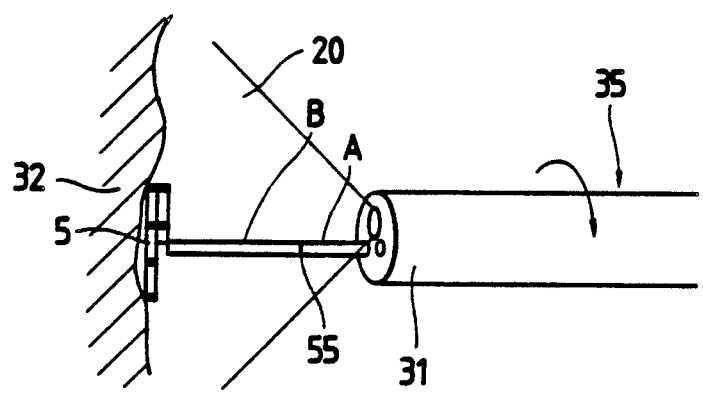
FIG. 20 is a fragmentary schematic view showing the operation of the length-measuring device of the sixth embodiment.

When the orientation of the length-measuring portion 5 (disposed in its generally T-shaped condition as shown in FIG. 20) with respect to the field of vision is not good, so that the observation of the length-measuring portion 5 can not be suitably carried out, the whole of the endoscope 35 is rotated. Usually, this rotation is effected by manipulating an endoscope operating portion (not shown) provided at the proximal side.

At this time, the portion A of the tube 1, disposed rearwardly of the cut portion 55 and mostly received in the forceps channel, is rotated together with the endoscope 35. However, since the length-measuring portion 5, defined as the distal end portion of the tube 1, is pressed against the affected part 32, the portion B disposed forwardly of the cut portion 55 is not rotated together with the endoscope 35. At this time, although the operating core rod 7 is rotated together with the endoscope 35, the pulling wire 10 is not twisted since its tied portion 10a in the form of a loop is loosely fitted on the operating core rod 7.

Thus, when the whole of the endoscope 35 is rotated, the length-measuring portion 5 is not rotated, and therefore the orientation of the length-measuring portion 5 with respect to the field of vision is changed within the field of vision. Thus, the orientation of the length-measuring portion 5 can be suitably changed to enable a clear observation of the length-measuring portion 5 in the field of vision.

As a modified form of the sixth embodiment, the first slit 2 and the second slit 6 can be arranged in the manner as described above for the second embodiment (FIG. 6).

In the length-measuring device for an endoscope according to the sixth embodiment, even when the tube approaches the target affected part in a direction oblique thereto, the length-measuring portion can be easily brought into intimate contact with the affected part, and the size of the affected part can be measured. In addition, simple operations are only needed when using and removing the length-measuring device. Further, the orientation of the T-shaped length-measuring portion with respect to the field of vision can be easily changed, and therefore the orientation of the length-measuring portion can be suitably changed in the field of vision to enable a clear observation of the length-measuring portion to achieve an accurate measurement.

Among treatment instruments adapted to be inserted into a forceps channel in an endoscope, the most frequently used for a long time is a forceps for picking up a living tissue. Generally, after such a forceps picks up a living tissue to be examined, the forceps is immediately and quickly withdrawn from the forceps channel. For this reason, in many cases, a length-measuring device is, after use, also quickly withdrawn from the forceps channel.

In the length-measuring device for an endoscope according to the first embodiment, immediately after the measuring operation, the pulling wire 10, connected to the distal end portion of the tube 1 being kept in a generally T-shaped condition, is kept tense or taut. Therefore, when trying to withdraw the length-measuring device from the forceps channel too quickly, the T-shaped distal end portion may become engaged with the forceps channel and fail to be returned into a straight condition along the forceps channel, which may result in damage to the pulling wire 10 and the tube 1.

Length-measuring devices according to seventh to ninth embodiments of the invention overcome such problems, and are of such a construction that the length-measuring portion can be easily brought into intimate contact with the affected part even in a direction oblique to the affected part to enable a measurement at the center of the field of vision and that, after the measuring operation, the length-measuring device can be quickly withdrawn from the forceps channel in the endoscope.

Figure 21:
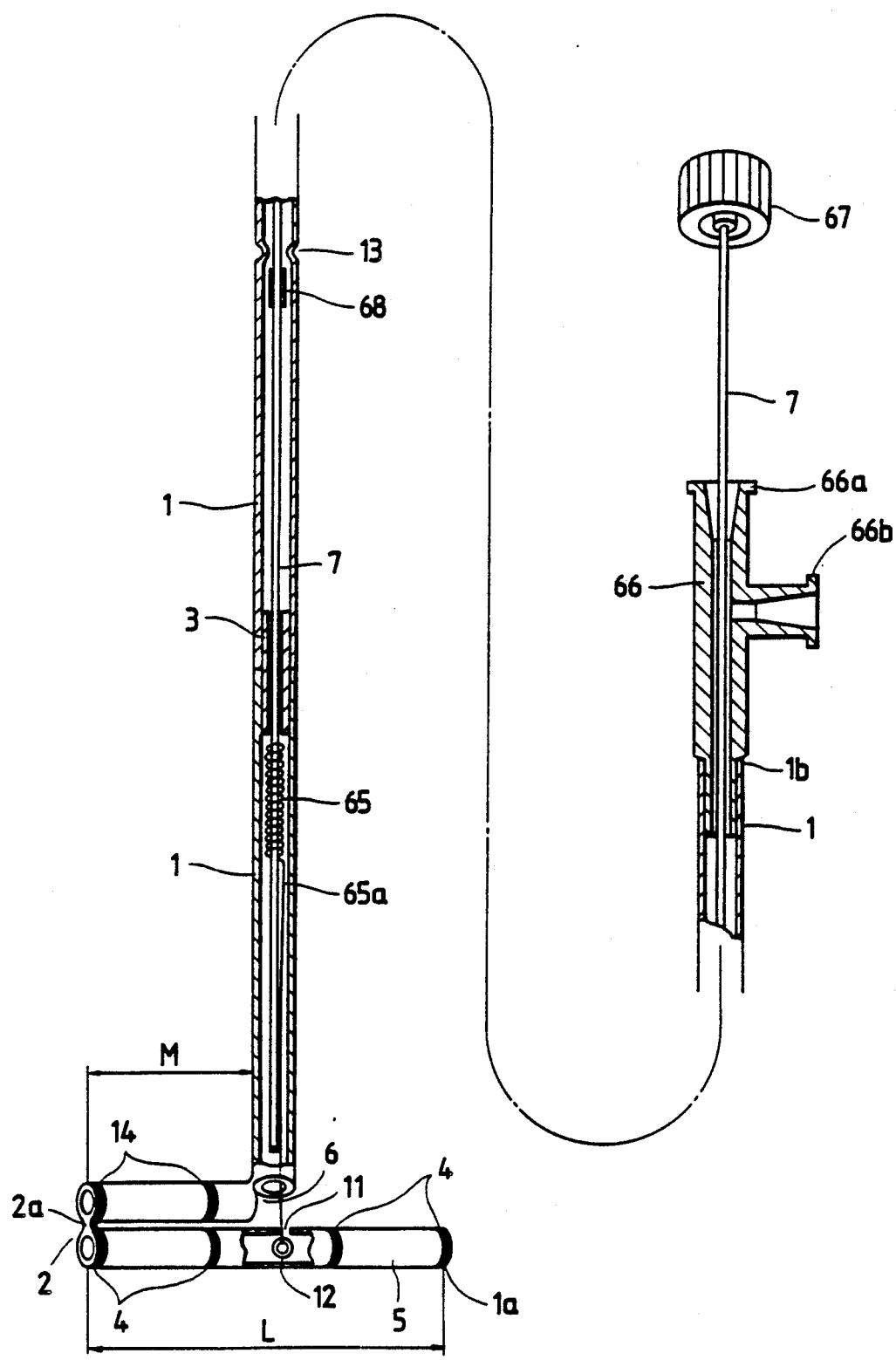
FIG. 21 is a view similar to FIG. 2, but showing a length-measuring device according to a seventh embodiment of the invention.
Figures 22, 23:
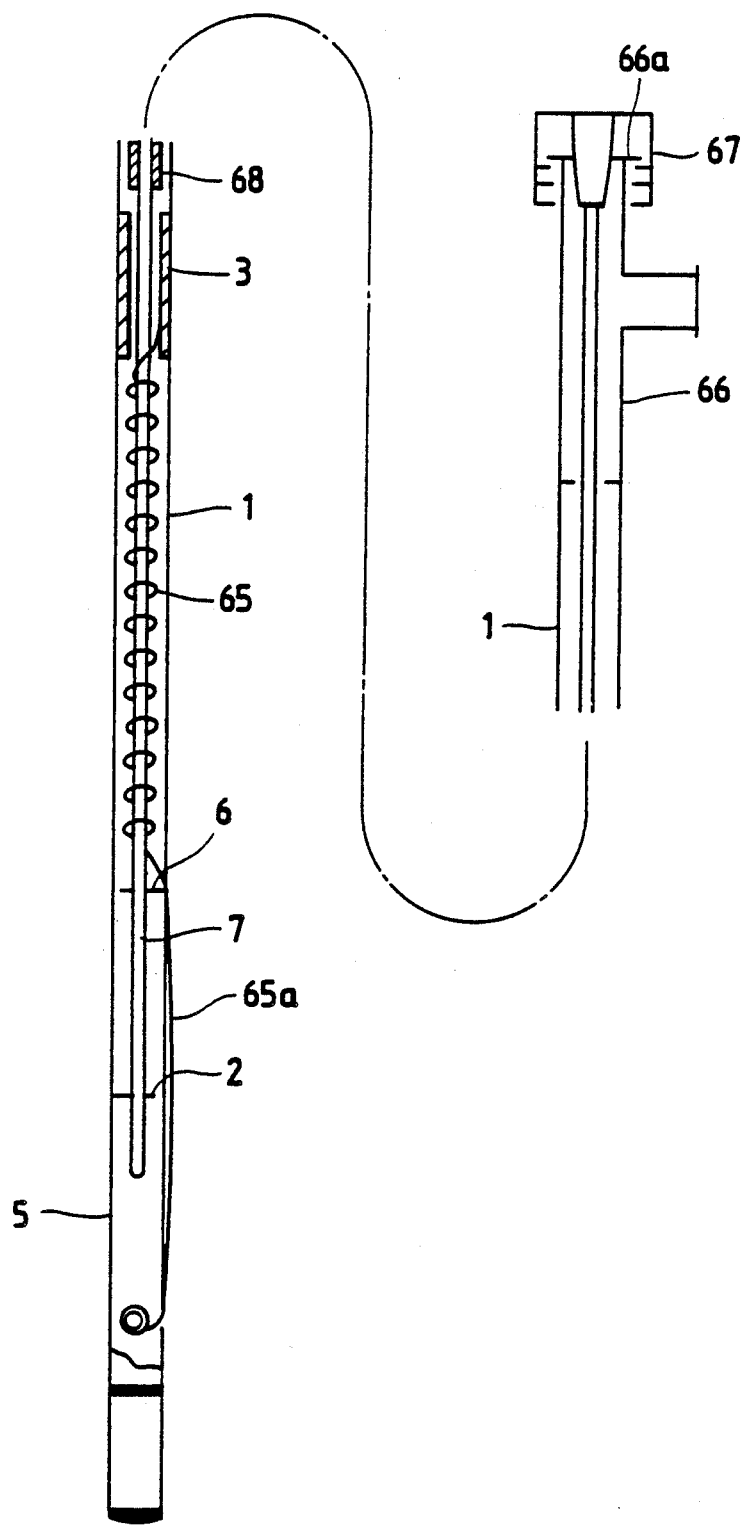
FIG. 22 is an enlarged cross-sectional view of a portion of the length-measuring device of the seventh embodiment.
FIG. 23 is a schematic view of the length-measuring device of the seventh embodiment being inserted into a forceps channel in the endoscope.

The seventh embodiment shown in FIG. 21 is based on the third embodiment (FIG. 9) and differs therefrom in the following points:

The tube 1 is cut transversely therethrough at its portion spaced a distance of 10 to 50 cm from its distal end. A connecting pipe 3 of metal is fixedly fitted in those portions of the tube 1 which are located immediately adjacent to this cut portion on opposite sides of the cut portion, to connect the two parts of the tube 1 into a single form. FIG. 22 is an enlarged fragmentary view showing such a connection by the connecting pipe 3. As is seen from FIG. 22, a spiral groove 1s is formed in the inner peripheral surface of each of those portions of the tube 1 immediately adjacent to the cut portion, so that an adhesive can be adequately applied to the outer peripheral surface of the connecting pipe 3.

As shown in FIG. 21, scale marks 14 corresponding to the scale marks 4 are also formed on the outer peripheral surface of that portion of the tube 1 extending between the first slit 2 and the second slit 6.

A mouthpiece 66 made of a synthetic resin or metal is fixedly connected to the proximal end 1b of the tube 1, and communicates with the tube 1. The mouthpiece 66 has a first Luer lock fitting 66a formed at its proximal end and disposed coaxially with the tube 1, and a second Luer lock fitting 66b formed on and extending perpendicularly from the outer peripheral surface of the mouthpiece 66. A syringe (not shown) or the like is adapted to be fitted in the second Luer lock fitting 66b to supply a cleaning liquid into the tube 1 to clean or sterilize the interior of the tube 1.

A manipulation thumbpiece 67 can be releaseably fitted in the first Luer lock fitting 66a, and the core rod 7 is fixedly secured at its proximal end to the thumbpiece 67. By pushing and pulling the manipulation thumbpiece 67, the core rod 7 is moved forward and backward in the tube 1, respectively.

A stopper 68, for example in the form of a metal pipe or a synthetic resin tube is fixedly mounted on the core rod 7 in an intermediate position between the opposite ends of the core rod 7, the stopper 68 being fixed to the core rod 7 by an adhesive or by pressing. When the manipulation thumbpiece 67 is pulled so that the distal end of the core rod 67 is retracted to a position located rearwardly of the second slit 6 as shown in FIG. 21, the stopper 68 is brought into engagement with the constricted portion 13 of the tube 1 to thereby prevent a further backward movement or retraction of the core rod 7. When the manipulation thumbpiece 67 is fitted in the first Luer lock fitting 66a, the distal end of the core rod 7 passes past the first slit 2 into the length-measuring portion 5 as shown in FIG. 23. Thus, the distal end of the core rod 7 is movable between the position located adjacent to and rearwardly of the second slit 6 and the position located adjacent to and forwardly of the first slit 2. A coil spring 65 is mounted within that portion of the tube 1 located forwardly of the connecting pipe 3, and is wound around the core rod 7. As best shown in FIG. 22, the proximal end of the coil spring 65 is fixedly secured to the connecting pipe 3 by silver-alloy brazing or the like. A pulling wire 65a made, for example, of a silkworm gut is connected to the distal end of the coil spring 65. The pulling wire 65a may be formed by a straightened distal portion of the coil spring 65 of a greater length. The pulling wire 65a extends outwardly from the tube 1 through the second slit 6, and passes through the hole 11 formed through the peripheral wall of the length-measuring portion 5, and is tied to the retainer ring 12 disposed within the length-measuring portion 5, the through hole 11 being provided at the central portion of the length-measuring portion 5.

With this construction, when the core rod 7 is disposed rearwardly of the second slit 6 so that the tube 1 can be bent at the first and second slits 2 and 6 as shown in FIG. 21, the length-measuring portion 5 is urged toward the second slit 6 by the resilient force of the coil spring 65. In this condition, the tube 1 is bent at the first and second slits 2 and 6 so that the distal end portion of the tube 1 assumes a T-shape. When the core rod 7 is pushed beyond the first slit 2, the tube 1 is straightened by the core rod 7 as shown in FIG. 23. At this time, the coil spring 65 is axially extended against its resilient force. However, as shown in FIG. 23, the pulling wire 65a is sufficiently long that the coil spring 65, when extended, will not project outwardly of the tube 1 through the second slit 6.

The manner of using the length-measuring device for an endoscope according to the seventh embodiment will now be described.

First, the core rod 7 is inserted into the tube 1 to such an extent that its distal end is disposed within the length-measuring portion 5, as shown in FIG. 23. In this condition, since the core rod 7 is passed past the second and first slits 6 and 2, the tube 1 can not be bent at the slits 2 and 6. Therefore, the length-measuring device in this condition can be easily inserted through the forceps channel in the endoscope.

When the distal end portion of the tube 1 is projected from the distal end of the endoscope, the manipulation thumbpiece 67 is pulled. As a result, the core rod 7 is retracted past the first slit 2 and the second slit 6, and the length-measuring portion 5 is pulled by the coil spring 65, so that the distal end portion of the tube 1 assumes a T-shape. In this condition, when the length-measuring portion 5 is pressed against the target affected part, the length-measuring portion 5 is always observed at the center of the field of vision, and the size of the affected part can be read by means of the scale marks 4 and 14.

Figure 24:
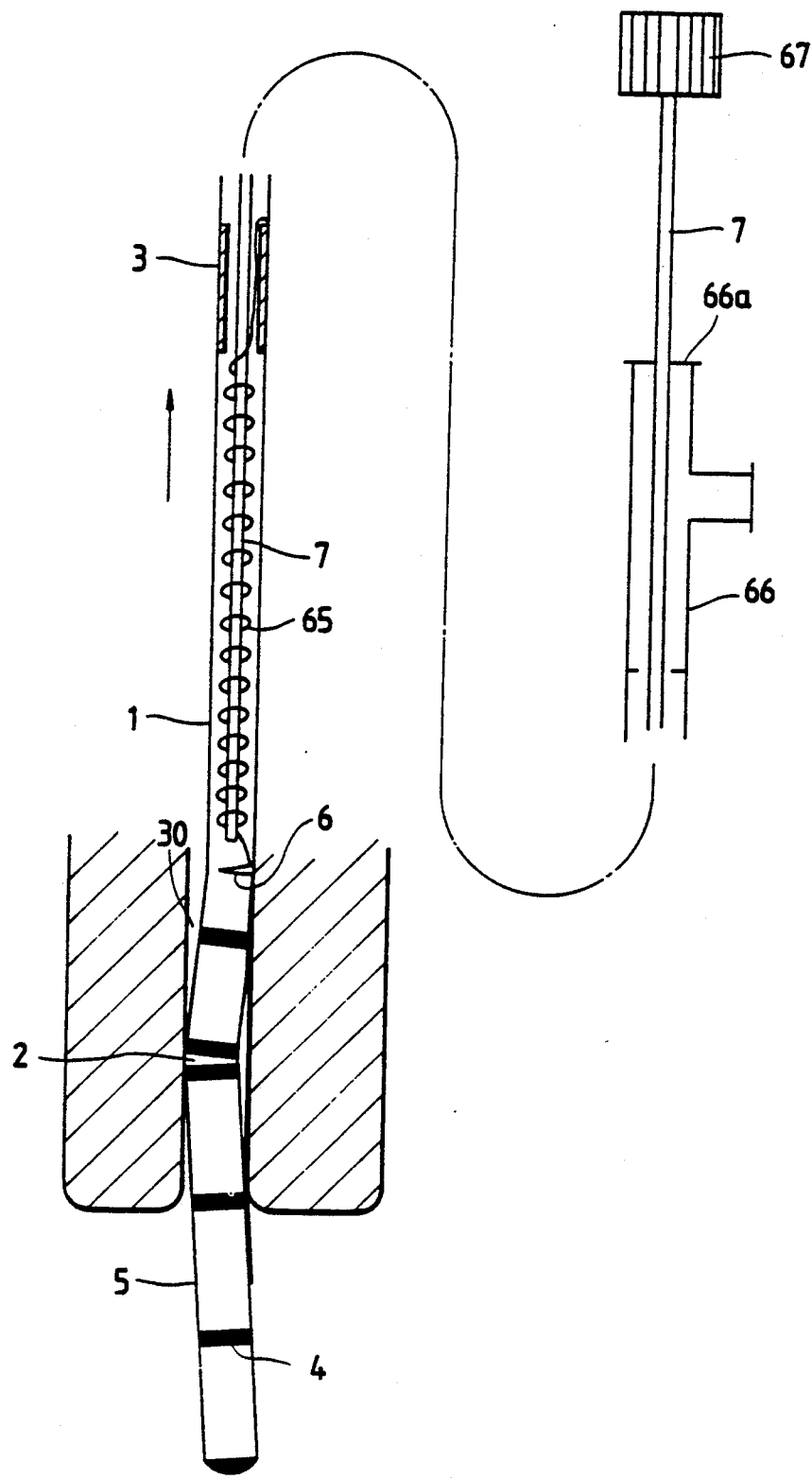
FIG. 24 is a schematic view of the length-measuring device of the seventh embodiment being withdrawn from the forceps channel.

All that has to be done for withdrawing the length-measuring device from the forceps channel 90 in the endoscope after use of the device is merely to pull or retract the tube 1 from its measuring position shown in FIG. 21 toward the proximal side. As a result, the T-shaped distal end portion of the tube 1 is returned by itself into a straight condition along the forceps channel 30 as shown in FIG. 24, and in accordance with this straightening of the tube 1 the coil spring 65 is extended. Therefore, even when the tube 1 is withdrawn very quickly, the distal end portion of the tube 1 is straightened by this withdrawal with the coil spring 65 being correspondingly extended, thus enabling such a quick withdrawal.

As a modified form of the seventh embodiment, the first slit 2 and the second slit 6 can be arranged in the manner as described above for the second embodiment (FIG. 6).

FIG. 25 shows the eighth embodiment of the invention. In this embodiment, the stopper 68 is fixedly mounted on the core rod 7 adjacent to the distal end of the core rod 7. A rubber string 62 is connected at one end to the core rod 7 adjacent to and rearwardly of the stopper 68, and the other end of the rubber string 62 is connected to the ring 12 disposed within the length-measuring portion 5. Except for these parts, this embodiment is of the same construction as that of the seventh embodiment. In this embodiment, in use, the core rod 7 is pulled or retracted toward the proximal side so that the rubber string 62 is pulled into the tube 1, and the length-measuring portion 5 is urged toward the second slit 2 by the resilient force of the rubber string 62. After use, when the length-measuring device is withdrawn from the forceps channel, the distal end portion of the tube 1 is straightened in the forceps channel, and in accordance with this straightening operation the rubber string 62 is extended.

FIG. 26 shows the ninth embodiment of the invention in which the rubber string of the eighth embodiment is replaced by a pulling wire 63 having no elasticity or resiliency such as a silkworm gut, and instead the core rod 7 is cut transversely therethrough at an intermediate position between the opposite ends thereof and the opposed cut portions of the core rod 7 are connected together by a coil spring 64. In this embodiment, when the core rod 7 is pulled toward the proximal side, the pulling wire 65 is pulled into the tube 1, so that the length-measuring portion 5 is urged toward the second slit 6 by the resilient force of the coil spring 64. After use, when the length-measuring device is withdrawn from the forceps channel in the endoscope, the distal end of the tube 1 is straightened in the forceps channel, and in accordance with this straightening operation the coil spring 64 is extended.

In the length-measuring devices for an endoscope according to the seventh to ninth embodiments, even when the tube approaches the target affected part in a direction oblique thereto, the length-measuring portion can be easily brought into intimate contact with the affected part, and the size of the affected part can be measured at the center of the field of vision. In addition, simple operations are only needed when using the length-measuring device. Further, after use, when the length-measuring device is to be withdrawn from the forceps channel, all that has to be done is to merely pull the tube, and therefore the length-measuring devices can be withdrawn quite quickly.

In the length-measuring device for an endoscope according to the first embodiment, when the pulling wire is pulled toward the proximal side, the tube is bent or turned 180 degrees at the first slit. Then, when the distal end of the tube is pressed against the target affected part 32 as shown in FIG. 27, the tube is bent or folded into a T-shape at the second slit 6 as indicated in phantom in FIG. 27, so that the length-measuring portion 5 is held in intimate contact with the affected part 32, thus enabling a measurement of the size of the affected part.

However, in the length-measuring device according to the first embodiment, unless the tube is pressed against the affected part, the distal end portion of the tube is not brought into a T-shape Therefore, the operation of the length-measuring device of the first embodiment is rather cumbersome, and whether the distal end portion of the tube can be easily bent into a T-shape or not is dependent on its orientation. In addition, once the length-measuring device is brought out of contact with the affected part, next time the device must be operated again. Further, since the slit is pressed against the affected part in the axial direction of the tube, the tube rubs on the affected part, which may cause bleeding or an ulcer.

Length-measuring devices for an endoscope according to tenth and eleventh embodiments of the invention overcome such problems and are of such a construction that the length-measuring portion can be brought into contact with the affected part even in a direction oblique thereto to thereby enable a measurement at the center of the field of vision, and that a measuring operation can be easily carried out without the risk of damaging the affected part and other parts.

The tenth embodiment shown in FIG. 28 is based on the seventh embodiment (FIG. 21) and differs therefrom in the following points:

The tube 1 has a pair of first and second through holes 8a and 8b formed through the peripheral wall thereof and disposed respectively on opposite sides of the connective section 6a interrupting the second slit 6, the pair of through holes 8a and 8b being disposed substantially symmetrically with respect to the connective section 6a. The pulling wire 65a is loosely passed through the second and first through holes 8b and 8a, and is disposed exteriorly of the tube 1 between the two holes 8a and 8b.

Figure 29:
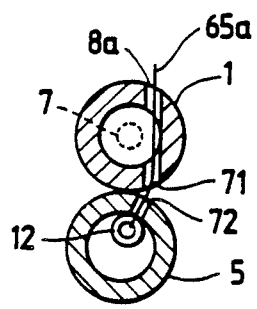
FIG. 29 is a cross-sectional view taken along the line V—V of FIG. 28.

A third through hole 71 is formed through the peripheral wall of the tube 1 in opposed relation to the first through hole 8a which is disposed forwardly of the second slit 6, and the pulling wire 65a again extends outwardly from the tube 1 through the third through hole 71 and is retained on the portion of the length-measuring portion 5 disposed in symmetrical relation to the third through hole 71 with respect to the connective section 2a interrupting the first slit 2. More specifically, the pulling wire 65a is passed through a through hole 72 formed through the peripheral wall of the length-measuring portion 5 near its center and is connected at its distal end to the retainer ring 12 disposed within the length-measuring portion 5. As shown in FIG. 29, the axes of the aligned first and third through holes 8a and 71 are adapted not to intersect the axis of the tube 1 so that the pulling wire 65a will not interfere with the movement of the core rod 7.

With this construction, when the core rod 7 is disposed rearwardly of the second slit 6 and the tube 1 can be bent at the first and second slits 2 and 6 (FIG. 28), the length-measuring portion 5 is urged toward the second slit 6 by the resilient force of the coil spring 65 through the pulling wire 65a. As a result, the tube 1 is bent at the first and second slits 2 and 6, so that the distal end portion of the tube 1 is bent or folded into a T-shape. In this embodiment, the pulling wire 65a is passed exteriorly of the tube 1 astride the connective section 6a and the connective section 2a. Therefore, when the pulling wire 65a is pulled toward the proximal side, the distal end portion of the tube 1 is pulled and positively folded into a T-shape.

Figure 30:
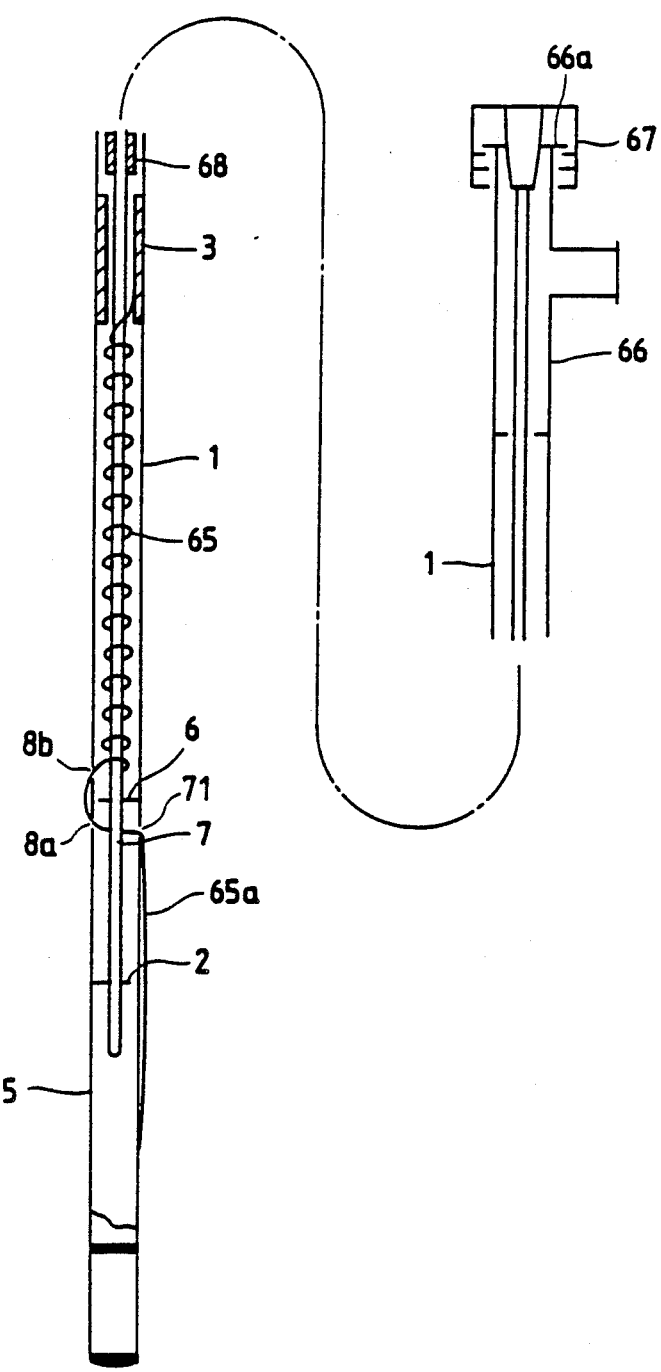
FIG. 30 is a schematic view of the length-measuring device of the tenth embodiment being inserted into a forceps channel in the endoscope.

When the core rod 7 is pushed to be disposed forwardly of the first slit 2 with the manipulation thumbpiece 66a fitted in the Luer lock fitting 66a, the tube 1 is straightened by the core rod 7 as shown in FIG. 30. At this time, the coil spring 65 is axially extended against its resilient force. However, as shown in FIG. 30, the pulling wire 65a is sufficiently long that the coil spring 65, when extended, will not project outwardly of the tube 1 through the second slit 6.

Figure 31:
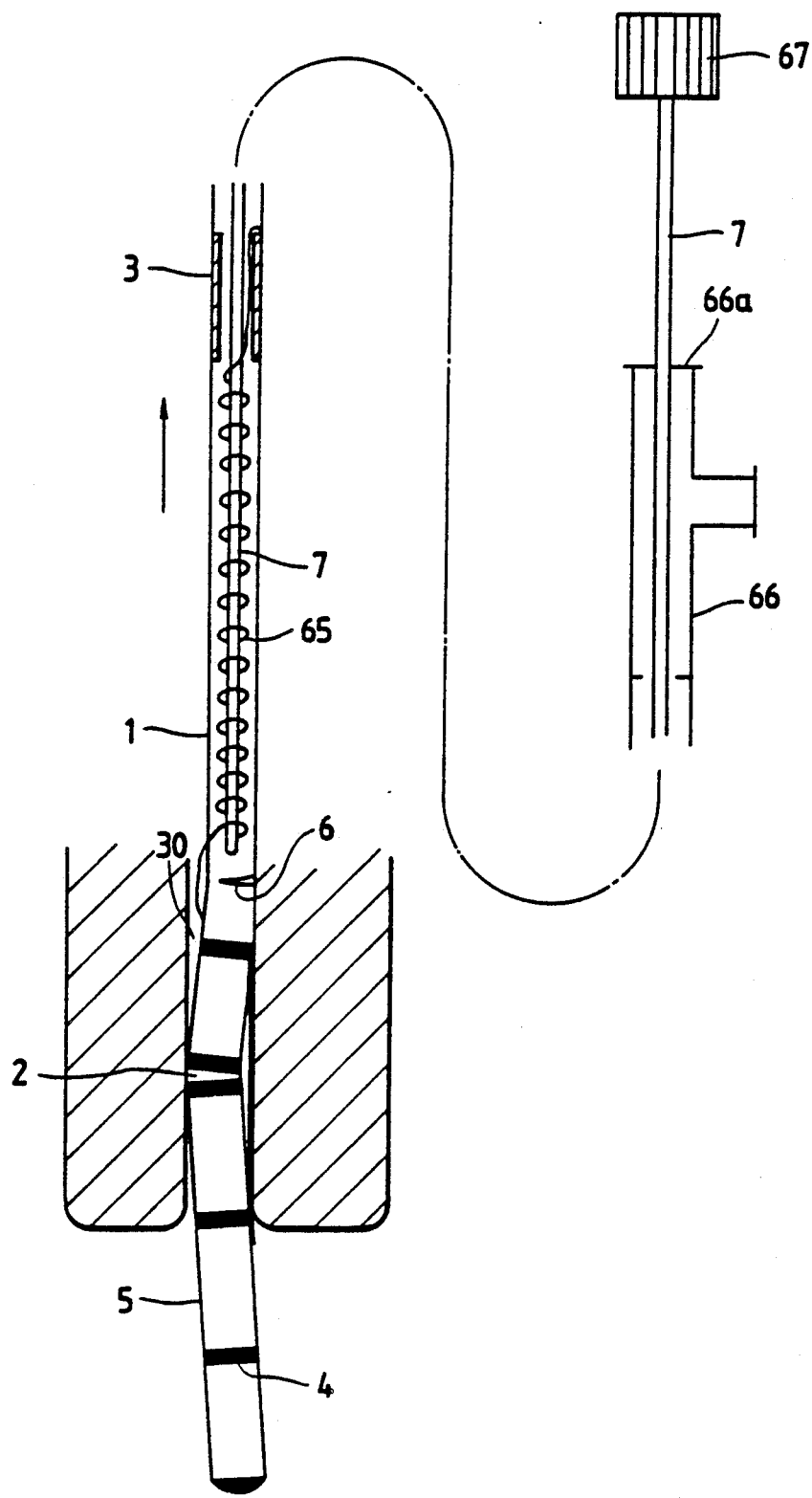
FIG. 31 is a schematic view of a length-measuring device according to an eleventh embodiment of the invention being withdrawn from the forceps channel in the endoscope.

All that has to be done for withdrawing the length-measuring device from the forceps channel 30 in the endoscope after use of the device is merely to pull or retract the tube 1 from its measuring position (FIG. 28) toward the proximal side. As a result, the T-shaped distal end portion of the tube 1 is returned by itself into a straight condition along the forceps channel 30 as shown in FIG. 31, and in accordance with this straightening of the tube 1 the coil spring 65 is extended. Therefore, even when the tube 1 is withdrawn very quickly, the distal end portion of the tube 1 is straightened in accordance with this withdrawal with the coil spring 65 being correspondingly extended, thus enabling such a quick withdrawal.

Figure 32:
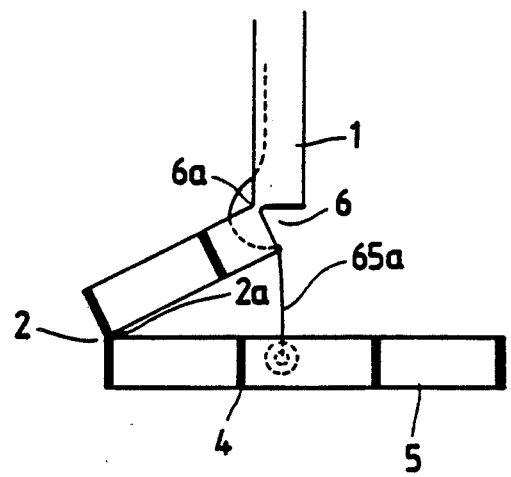
FIG. 32 is a side-elevational view of a distal end portion of the length-measuring device of the eleventh embodiment.
Figure 33:
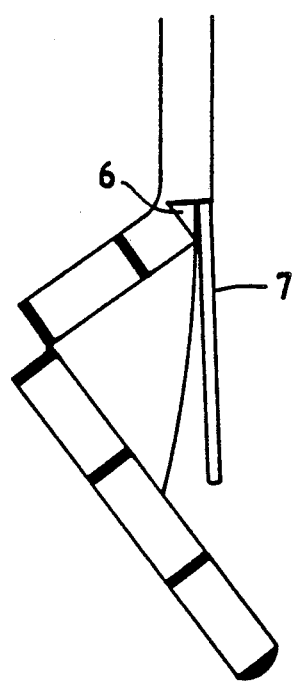
FIG. 33 is a fragmentary side-elevational view showing the length-measuring device of the first embodiment in its actual use.

FIG. 32 shows the eleventh embodiment of the invention in which the third through hole is not provided, and instead the pulling wire 65 extends outwardly of the tube 1 through the second slit 6 and is connected to the retainer ring 12. Except for this, the eleventh embodiment is of the same construction as that of the tenth embodiment.

As understood from the tenth and eleventh embodiments, in so far as the pulling wire 65a is passed exteriorly of the tube 1 astride the connective section 6a and the connective section 2a, any manner of passing the pulling wire 65 to the retainer ring 12 may be employed. For example, the through hole 71 in the tenth embodiment may be disposed closer to the first slit 2.

Also, the pulling wire 65a may be of any type and, for example, be of the type as described above for the first embodiment, in which the pulling wire is pulled from the proximal side.

In the length-measuring devices for an endoscope according to the tenth and eleventh embodiments, even when the tube approaches the target affected part in a direction oblique thereto, the length-measuring portion can be easily brought into intimate contact with the affected part, and the size of the affected part can be measured at the center of the field of vision. In addition, the distal end portion of the tube defining the length-measuring portion can be accurately and easily folded into a T-shape upon pulling of the pulling wire, and therefore the length-measuring devices can be quite easily operated. Further, since the distal end portion of the tube is folded into a T-shape, the distal end of the tube is not brought into contact with the affected part, thus eliminating the risk of damaging the affected part, which is quite advantageous from the viewpoint of safety.

In the length-measuring device of the first embodiment, the core rod is manually pulled or retracted. Therefore, there may be occasions when the core rod is insufficiently retracted and fails to be moved to a position rearwardly of the second slit, in which case the distal end portion of the tube is not formed into a T-shape.

Also, since the core rod 7 can be freely moved forward and backward, there may be occasions when the core rod 7 is inadvertently pushed or moved forward during use of the device, in which case the core rod 7 is projected outwardly of the tube 1 through the second slit 6, so that the tube 1 may not be returned to a straight condition. In such a case, when withdrawing the length-measuring device from the forceps channel, that portion of the tube 1 which is not returned to the straight condition may become engaged with the distal portion of the forceps channel and be broken, and this also may damage the wall of the body cavity of the patient.

A length-measuring device for an endoscope according to a twelfth embodiment of the invention overcomes such problems and is of such a construction that the length-measuring portion can be easily brought into intimate contact with the target affected part even in a direction oblique thereto, and that the distal end portion of the tube can be folded into a T-shape and the core rod is not kept projected from the slit in the tube to provide for safety.

Figure 34:
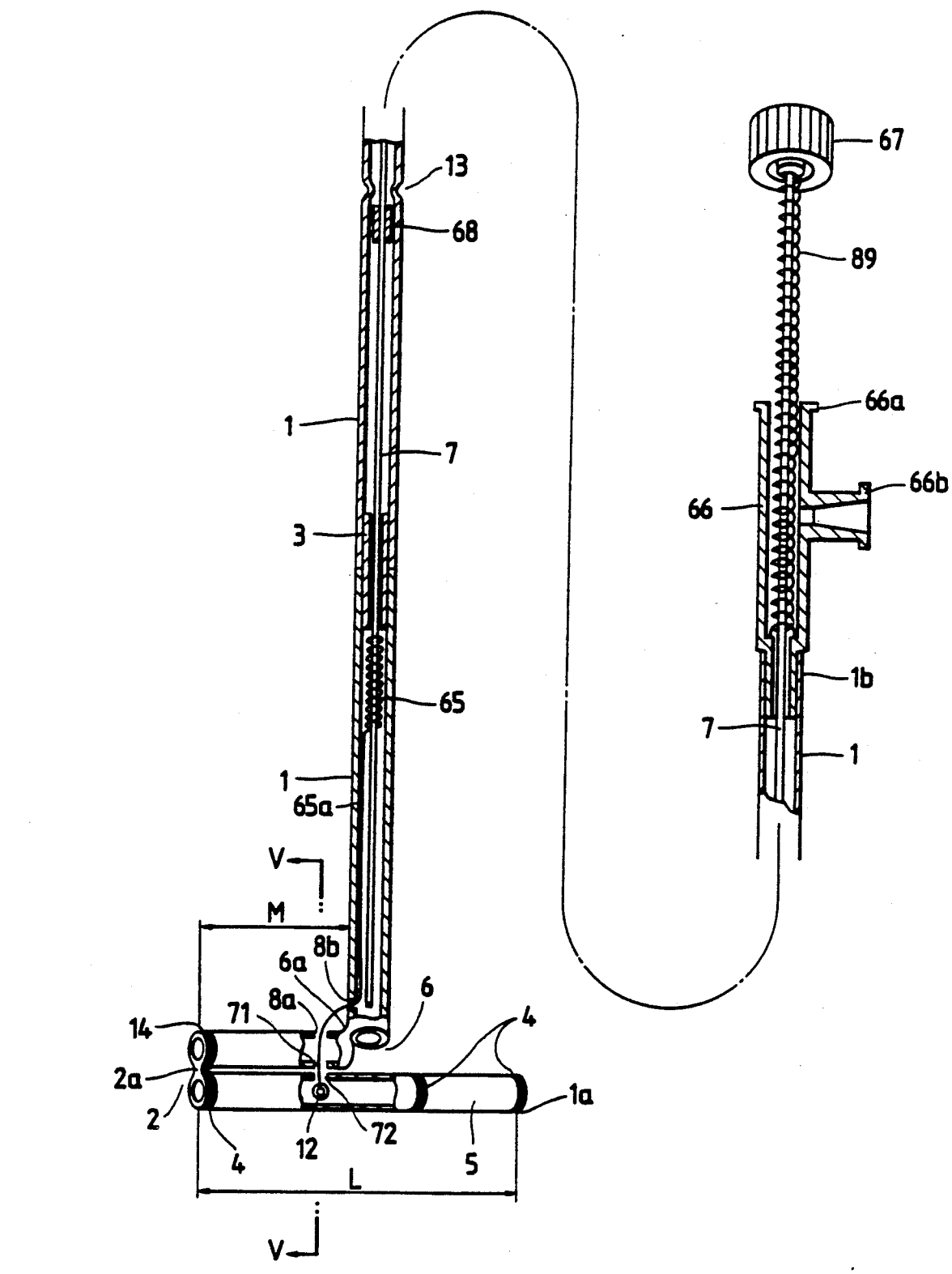
FIG. 34 is a view similar to FIG. 2, but showing a length-measuring device according to a twelfth embodiment of the invention.

The twelfth embodiment shown in FIG. 34 is based on the tenth embodiment (FIG. 28) and differs therefrom in the following points:

A coil spring 89 is wound in a compressed condition around the core rod 7 and extends between the manipulation thumbpiece 67 and the distal end of the mouthpiece 66. Therefore, the core rod 7 is normally urged by the coil spring 89 toward the proximal side (i.e., in a retracting direction). A stopper 68, for example in the form of a metal pipe or a synthetic resin tube, is fixedly mounted on the core rod 7 at an intermediate position between the opposite ends of the core rod 7, the stopper 68 being fixed to the core rod 7 by an adhesive or by pressing. In a free condition, the distal end of the core rod 7 is disposed adjacent to and rearwardly of the second slit 6, and the stopper 68 is held against the constricted portion 13 of the tube 1 to stop the core rod 7, as shown in FIG. 34.

The operation of the length-measuring device for an endoscope according to the twelfth embodiment will now be described.

Figure 35:
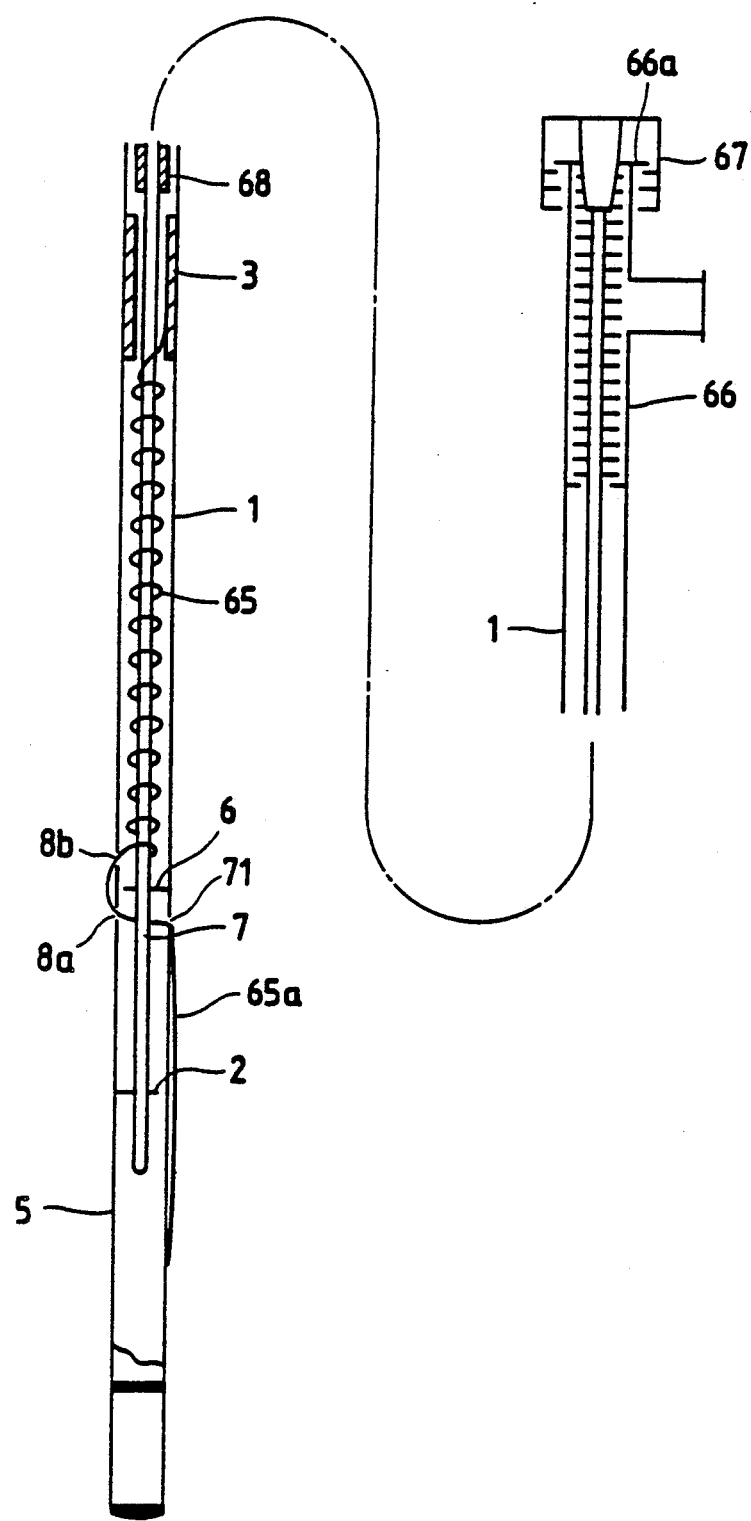
FIG. 35 is a schematic view of the length-measuring device of the twelfth embodiment being inserted into a forceps channel in the endoscope.

First, as shown in FIG. 35, the core rod 7 is inserted to such an extent that the core rod 7 is disposed within the length-measuring portion 6 of the tube 1 and the manipulation thumbpiece 67 is fitted in the Luer lock fitting 66a. In this condition, since the core rod 7 is passed past the second slit 6 and the first slit 2, the tube 1 is not bent or folded at the slits 6 and 2. Therefore, in this condition, the length-measuring device can be easily inserted through the forceps channel in the endoscope.

When the distal end portion of the tube 1 is projected from the distal end of the endoscope, the engagement between the manipulation thumbpiece 67 and the Luer lock fitting 66a is released. As a result, as shown in FIG. 34, the core rod 7 is moved toward the proximal side by the resilience of the coil spring 89, so that the core rod 7 is retracted past the first and second slits 2 and 6. Therefore, the length-measuring portion 5 is pulled or urged by the coil spring, so that the distal end portion of the tube 1 is folded or bent into a T-shape. In this condition, when the length-measuring portion 5 is moved toward the target affected part, the length-measuring portion 5 is always observed at the center of the field of vision and the size of the affected part can be read by means of the scale marks 4 and 14.

The engagement between the manipulation thumbpiece 67 and the Luer lock fitting 66a may be released when the distal end of the tube 1 is disposed in the forceps channel, in which case the distal end portion of the tube 1 is automatically bent at the slits 2 and 6 to assume a T-shape as soon as it is projected from the forceps channel to become spatially free.

Even if the manipulation thumbpiece 67 is inadvertently pushed during use of the device, the manipulation thumbpiece 67 is soon returned by the coil spring 89 to its state as shown in FIG. 34.

In the length-measuring device for an endoscope according to the twelfth embodiment, even when the tube approaches the target affected part in a direction oblique thereto, the length-measuring portion can be easily brought into intimate contact with the affected part, and the size of the affected part can be measured at the center of the field of vision. In addition, by releasing the engagement of the core rod-retaining means, the core rod is retracted past the first and second slits without fail and the tube is positively bent or folded at the first and second slits, so that the distal end portion of the tube assumes a T-shape, thus enabling a smooth measurement. Even if the core rod is inadvertently pushed during use of the device, the core rod is soon returned to its original condition or position, and therefore the core rod is not kept projected from the slit in the tube, thereby preventing damage to the device and the wall of the body cavity, thus providing for safety.

Figure 36:
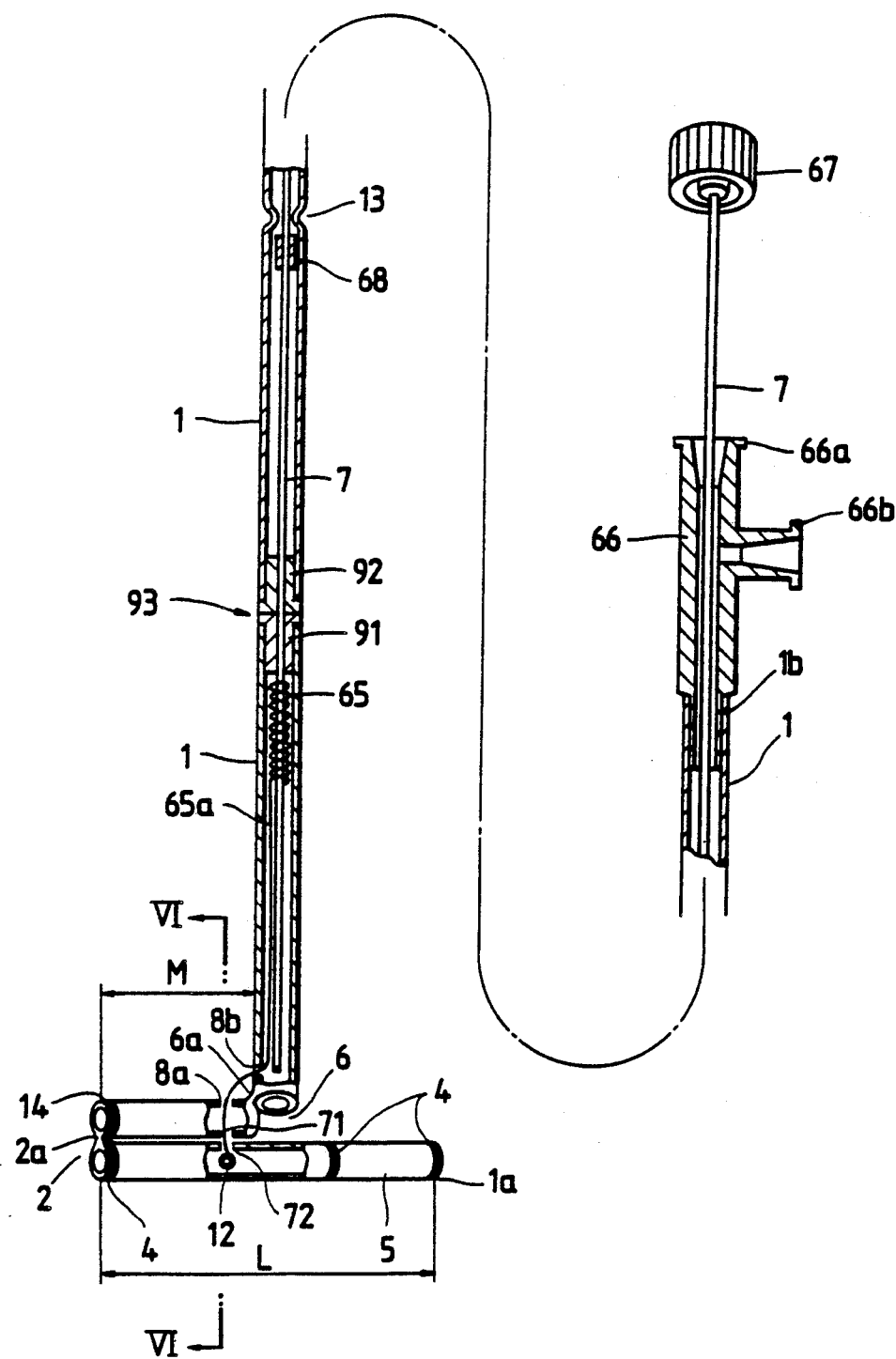
FIGS. 36 and 37 are views similar to FIG. 2, but showing a length-measuring device according to a thirteenth embodiment of the invention.
Figure 37:
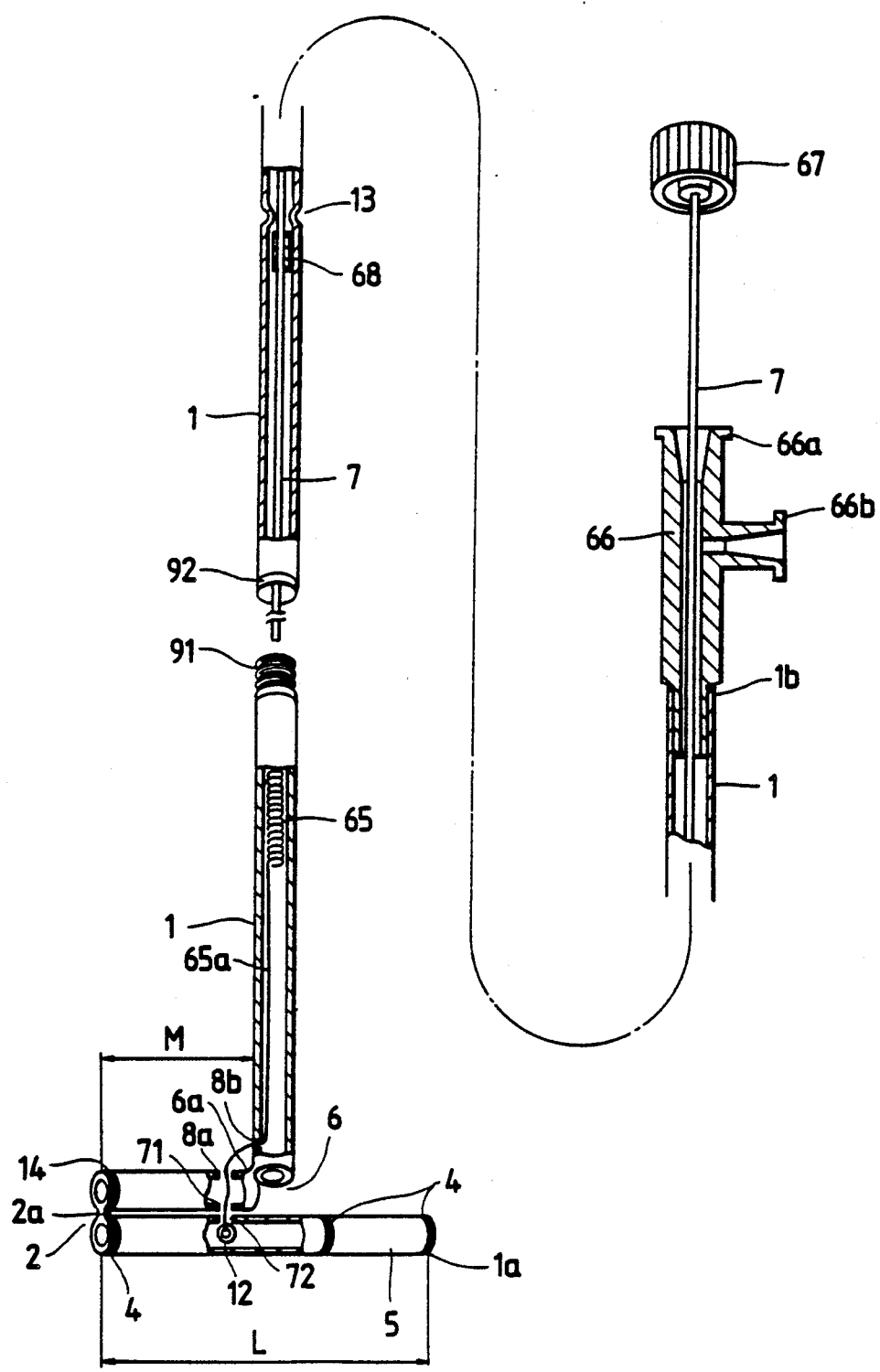

A thirteenth embodiment shown in FIGS. 36 and 37 is based on the tenth embodiment (FIG. 28) and differs therefrom in the following points:

In FIG. 36, the tube 1 is cut transversely therethrough at its portion spaced a distance of 10 to 50 cm from its distal end. Reference numeral 93 denotes this cut portion. Connecting pipes 91 and 92 are respectively fitted in and fixedly secured to those portions of the tube 1 located immediately adjacent to the cut portion 93 and on the opposite sides of the cut portion 93, and the connecting pipes 91 and 92 are connected together to form the tube 1 into a single form. This connected portion is schematically shown in FIG. 36 and is also shown in FIG. 38 with an enlarged scale. More specifically, the connecting pipe 91 has external threads 91a, and the connecting pipe 92 has internal threads 92a threadedly engaged with the external threads 91a, thus the two parts of the tube 1 are releaseably connected together at the cut portion 93. FIG. 39 shows the condition in which the two parts of the tube 1 are disconnected from each other at the cut portion 93.

A spiral groove 1s formed in the inner surface of each of those portions of the tube 1 located immediately adjacent to the cut portion 93, so that an adhesive can be adequately applied to the outer peripheral surface of each of the connecting pipes 91 and 92. The connecting pipes 91 and 92 may be connected by any suitable means other than the threaded connection arrangement in so far as such other means allows a releaseable connection between the pipes 91 and 92.

A coil spring 65 (resilient member) is provided within the tube 1 adjacent to the connecting pipe 91 and is wound around the core rod 7. The proximal end of the coil spring 65 is fixedly secured to the connecting pipe 91 by silver-alloy brazing or the like as shown in FIG. 38. A pulling wire 65a made, for example, of a silkworm gut is connected to the distal end of the coil spring 65. The pulling wire 65a may be a straightened distal portion of the coil spring 65 of a greater length.

In the length-measuring device of the thirteenth embodiment, by releasing the connection between the connecting pipes 91 and 92, the distal portion of the tube 1, which includes the length-measuring portion 5 and contains the coil spring 65, can be separated from the proximal portion of the tube 1. With this construction, depending on the parts of the body to be measured and the intended purposes, the tube distal portions having respective length-measuring portions 5 of different lengths can be exchanged. Also, when the length-measuring portion 5 is subjected to damage or malfunction, the tube distal portion can be replaced by a new one of the same size.

In the case of changing one distal portion of the tube 1 by another distal portion having the length-measuring portion 5 of a different length, when the distal portion is too short, the core rod 7 is engaged with the distal end portion of the tube 1, so that the distal portion of the tube can not be connected to the proximal portion of the tube 1 at the cut portion 93. In contrast, when the distal portion is too long, the core rod 7 does not reach the first slit 2, so that the distal end portion of the tube 1 can not be straightened. Taking these into account, the length of each exchangeable distal portion is suitably determined.

Figure 40:
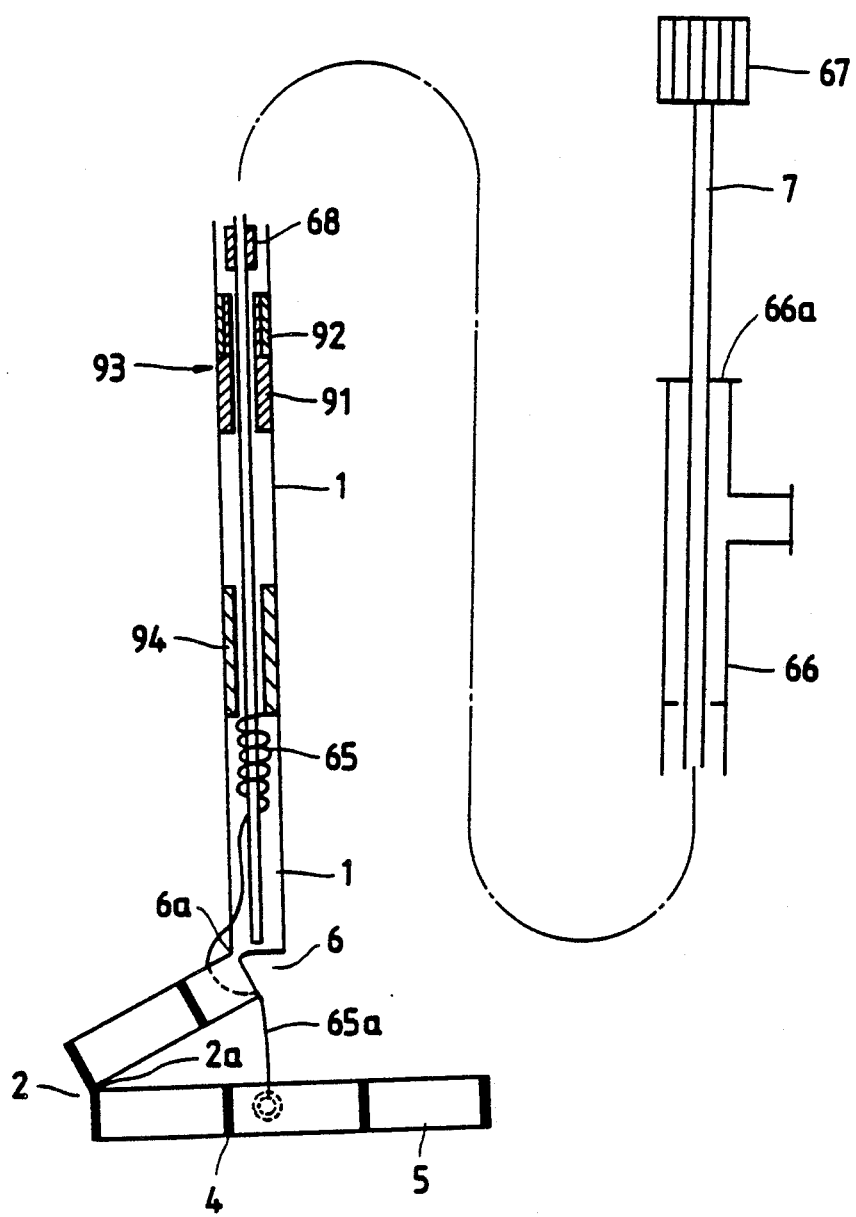
FIG. 40 is a schematic view of a length-measuring device according to a fourteenth embodiment of the invention.

FIG. 40 shows a fourteenth embodiment of the invention. In this embodiment, a cut portion 93 is provided at a position considerably away from the position toward the proximal side, in which the proximal end of the coil spring 65 is fixed relative to the tube 1, toward the proximal side. The connecting pipes 91 and 92 are threadedly connected together in a releasable manner, so that the distal portion of the tube can be changed as described above for the thirteenth embodiment. A pipe 94 is mounted within the tube 1 and fixedly secured thereto, and the proximal end of the coil spring 65 is fixedly secured to the pipe 94.

In the fourteenth embodiment of FIG. 40, the third through hole is not provided, and instead the pulling wire 65a is extended outwardly from the tube 1 through the second slit 6 and is connected at its distal end to the length-measuring portion 5. Details in the construction of the length-measuring portion 5 and its adjoining portion may be of any type.

In the length-measuring devices for an endoscope according to the thirteenth and fourteenth embodiments of the invention, the tube distal portions each having the length-measuring portion can be exchanged, and a desired one can be selected in accordance with the body part to be measured and the intended purposes. Further, when the length-measuring portion is subjected to malfunction, it is only required to replace the tube distal portion by a new one of the same size.

Thus, in the length-measuring devices for an endoscope according to the thirteenth and fourteenth embodiments, there is no need to provide a number of length-measuring devices, and the cost of using the length-measuring devices can be much reduced.

Figure 41:
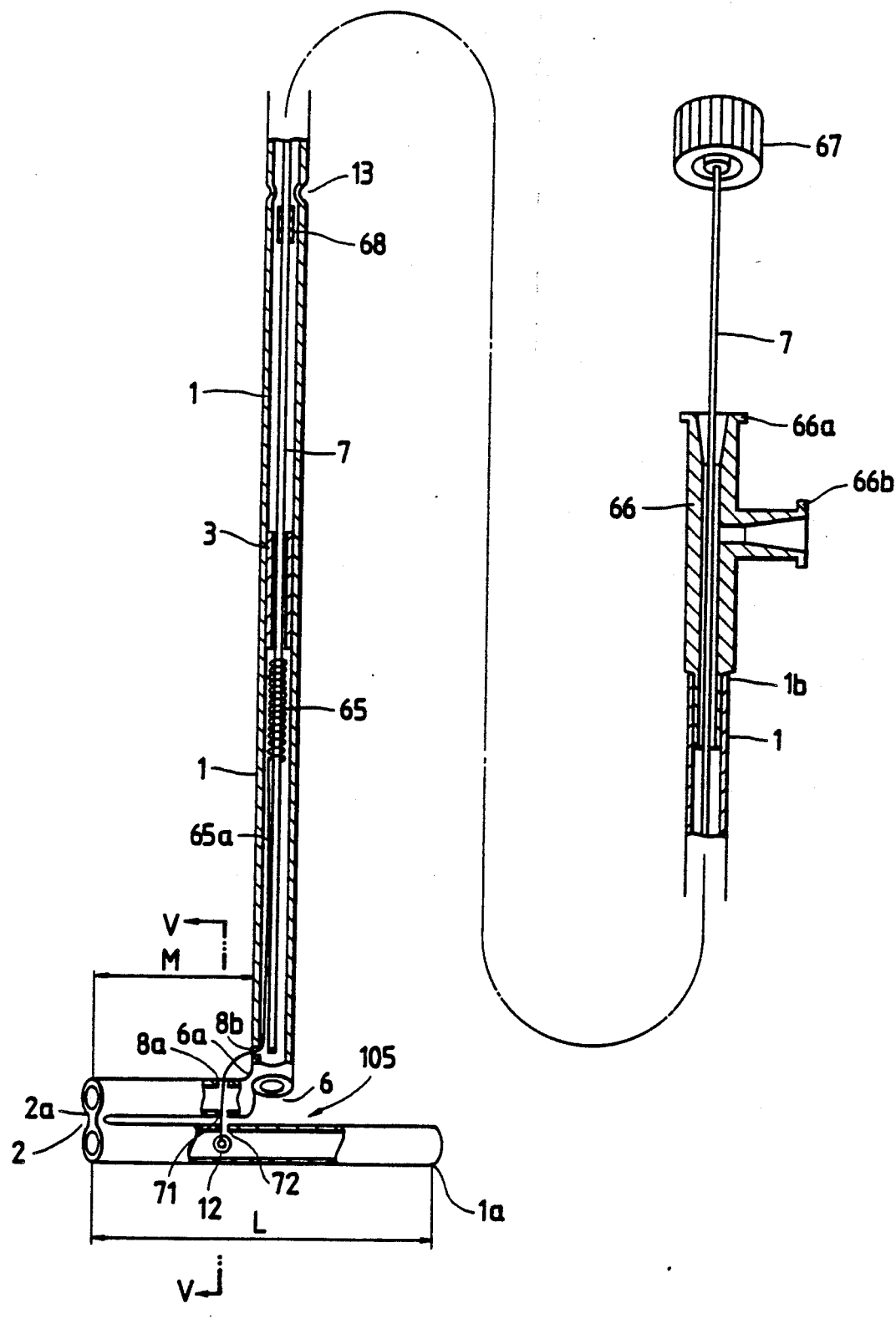
FIG. 41 is a partly cross-sectional view of a reference color display device for color tone adjustment for use with an endoscope according to a fifteen embodiment of the invention.
Figure 45:
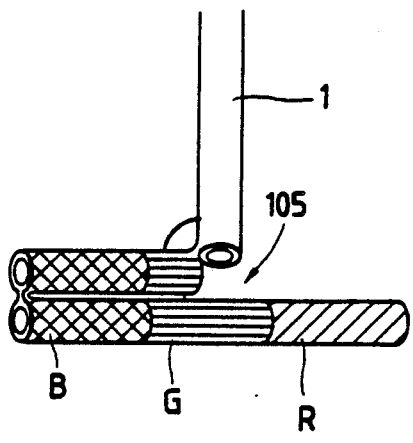
FIG. 45 is a perspective view of a distal end portion of the reference color display device of FIG. 41.

FIG. 41 shows a reference color display device for color tone adjustment according to a fifteenth embodiment of the invention which is based on the length-measuring device of the tenth embodiment (FIG. 28) and differs therefrom in the following points:

As shown in FIG. 45, the outer peripheral surface of the distal end portion 105 is colored in three primary colors, that is, red (R), green (G) and blue (B). The three colored sections of the outer peripheral surface have the same length. The three colors need not always be standard colors of the three primary colors.

The manner of using the reference color display device for color tone adjustment of the fifteenth embodiment will now be described.

Figure 42:
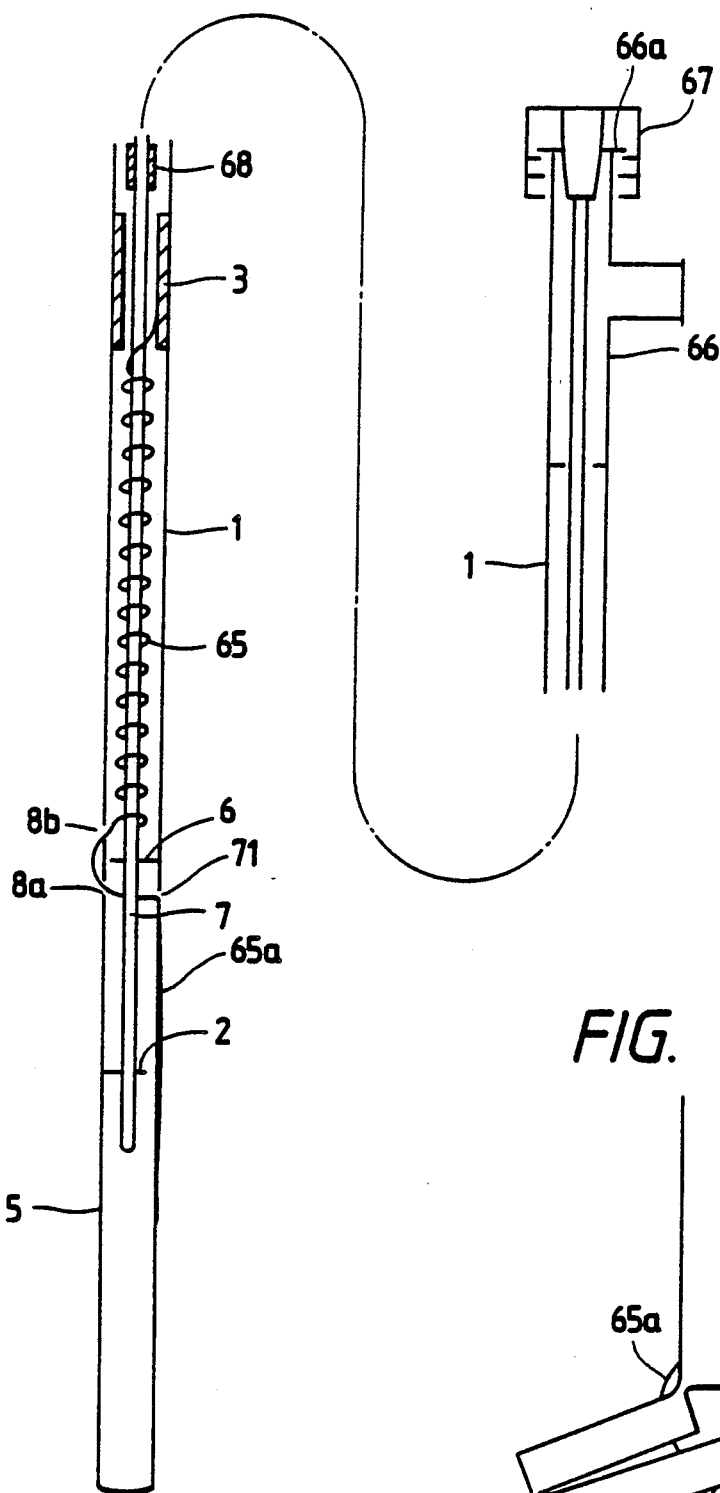
FIG. 42 is a schematic view of the reference color display device being inserted into a forceps channel in the endoscope.

First, as shown in FIG. 42, the core rod 7 is inserted into the tube 1 to such an extent that the distal end of the core rod 7 is disposed within the distal end portion 105 of the tube 1. In this condition, since the core rod 7 is passed past the second slit 6 and the first slit 2, the tube 1 can not be bent at the slits 2 and 6. Therefore, in this condition, the tube can be easily inserted through the forceps channel in the endoscope.

Then, the reference color display device for color tone adjustment is inserted through the forceps channel in the so-called electronic endoscope having a solid-state image pickup element for transmitting an observed image.

When the distal end portion of the tube 1 is projected from the distal end of the endoscope, the manipulation thumbpiece 67 is pulled. As a result, the core rod 7 is retracted or moved backward past the first slit 2 and the second slit 6, so that the distal end portion 105 is pulled by the coil spring 65 and is folded into a T-shape, as shown in FIG. 41.

In this condition, when the distal end portion 105 is pressed into intimate contact with the surface of the mucous membrane of the body cavity, the distal end portion 105 colored in the three reference colors (i.e., red, green and blue) is held generally flush with the surface of the mucous membrane, and the distal end portion 105 can be observed in the vicinity of the center of the field of vision. In this condition, while observing the picked-up image displayed on a monitor of the endoscope, the color tone of the image is adjusted so that the displayed three colors coincide with their respective actual colors. Thus, under the same conditions for an actual observation of the mucous membrane surface of the body cavity, the color tone adjustment can be carried out using the predetermined three primary colors as a reference.

In this embodiment, since the distal end portion 105 has the colored sections having the same length, these colored sections also serve as scale marks, and therefore the device can also be used as a length-measuring device for measurement within the body cavity.

Figure 43:
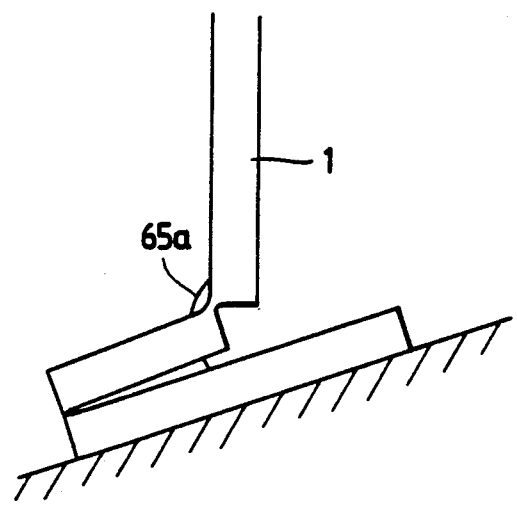
FIG. 43 is a side-elevational view of a distal end portion of the reference color display device being pressed against a surface of a mucous membrane.
Figure 44:
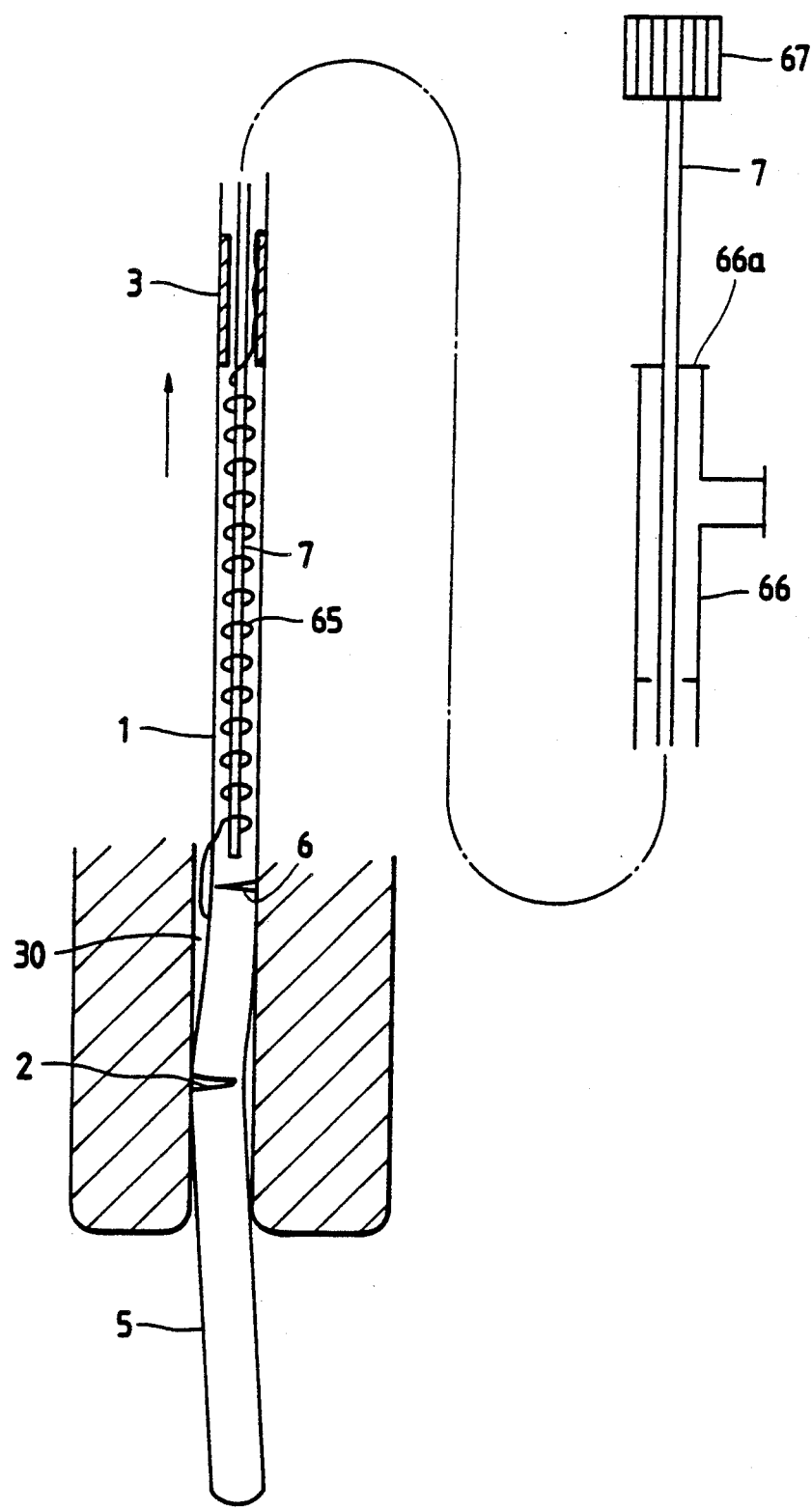
FIG. 44 is a schematic view of the reference color display device being withdrawn from the forceps channel.

When the tube 1 approaches the surface of the mucous membrane in a direction oblique thereto, the angle of bending of the tube 1 at the second slit 6 is changed merely by slightly pressing the side wall of the distal end portion 105 against the target surface of the mucous membrane, so that the distal end portion 105 is brought into intimate contact with the target surface (see FIG. 43). Thus, even when the tube 1 is approaching the surface of the mucous membrane in any direction oblique thereto, the distal end portion 105 can be positively brought into intimate contact with this surface.

For withdrawing the device from the forceps channel in the endoscope after use of the device, all that has to be done is to merely pull the tube 1 (which is in the condition shown in FIG. 41) toward the proximal side. As a result, the T-shaped distal end 105, when introduced into the forceps channel 90, is straightened by itself along the forceps channel 90, and in accordance with this straightening the coil spring 65 is extended. Therefore, even when the tube 1 is withdrawn very quickly, the distal end portion 105 is straightened in response to such withdrawing operation and is removed from the forceps channel, while extending the coil spring 65.

Figure 46:
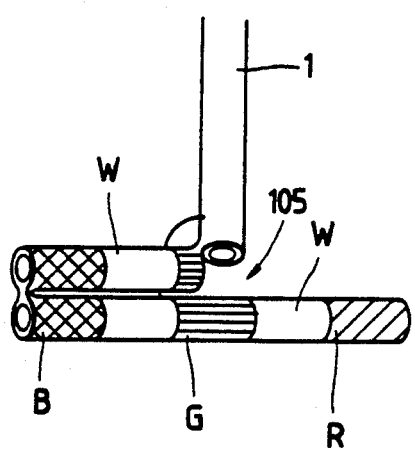
FIGS. 46 to 48 are views similar to FIG. 45, but showing modifications of the device of FIG. 41.

FIG. 46 shows a modified form of the invention in which white color sections (W) are interposed between the colored sections of the three primary colors, the white color sections having the same length as the colored sections of the three primary colors. With this arrangement, so-called white balance can be adjusted, and in addition the precision of the scale is enhanced.

Figure 47:
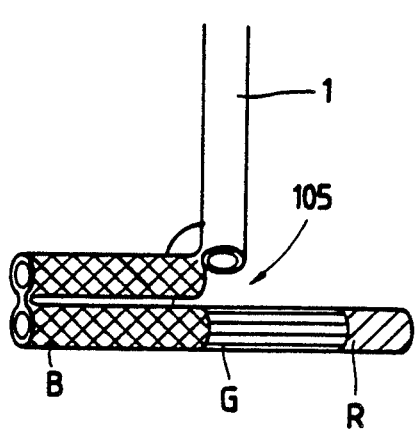

FIG. 47 shows another modified form of the invention in which the lengths of the colored sections of the three primary colors are varied in accordance with their color stimulus values. More specifically, the colored section of red which has a high color stimulus value is reduced in length, and in contrast the colored section of blue which has a low color stimulus value is increased in length. With this arrangement, the color adjustment precisions for the three primary colors can be at the same level. Since the colored sections have predetermined lengths, respectively, they can also be used as a scale of a length-measuring device.

Figure 48:
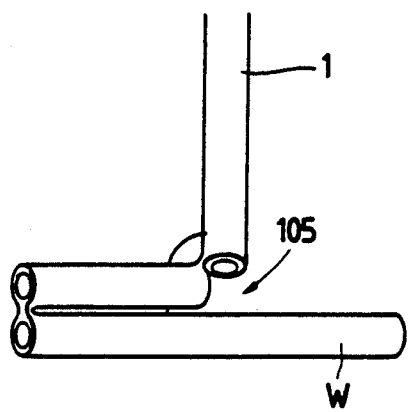

FIG. 48 shows a further modified form of the invention in which the whole of the distal end portion 105 of the tube 1 is colored in white. If the tube 1 itself has originally a white color, there is no need to color the tube. In this case, since the distal end portion 105 is entirely colored in white, it can be used to effect a white balance adjustment. Also, a scale can be formed on the distal end portion 105 so that it can also be used as a length-measuring means.

In the reference color display device for color tone adjustment according to the fifteenth embodiment, under the same conditions for an actual observation of the mucous membrane surface of the body cavity, the color tone adjustment of the observed image can be carried out using the predetermined reference colors. Therefore, the color tone of the observed image displayed on the monitor can be adjusted in an accurate and objective manner, and this enables a proper diagnosis.

When another part of the body is to be observed, the reference color display device for color tone adjustment according to the invention is inserted through the forceps channel, and the color tone is readjusted to match the environments of this new part of the body to be observed. This device can also serve as a length-measuring device for measuring the size of the mucous membrane surface of the body cavity and other parts of the body.

What is claimed is:

1. A length-measuring device for use with an endoscope, comprising:
   (a) a tube having a first slit formed therein and a second slit formed therein and disposed rearwardly of said first slit, said tube being bendable at each of said first and second slits, and said tube further having a length-measuring portion extending forwardly from said first slit to a distal end of said tube; and
   (b) means for bending said tube at said first and second slits.

2. A length-measuring device according to claim 1, in which said bending means comprises pulling means one end of which has a connecting relation with said length-measuring portion to pull said length-measuring portion.

3. A length-measuring device according to claim 2, in which said pulling means comprises an elongated member introduced into said tube from a portion of said tube other than said length-measuring portion, said elongated member being remotely operable at a proximal end of said tube so as to be pulled.

4. A length-measuring device according to claim 3, further comprising a core rod, and in which said elongated member is connected at its proximal end to a distal end of said core rod so as to be pulled via said core rod, said core rod being inserted into said tube from said proximal end of said tube.

5. A length-measuring device according to claim 4, in which said core rod has a spring member at a portion thereof.

6. A length-measuring device according to claim 3, in which said elongated member is a wire.

7. A length-measuring device according to claim 3, in which said elongated member is made of rubber.

8. A length-measuring device according to claim 3, in which said elongated member is introduced into said tube through said second slit.

9. A length-measuring device according to claim 3, in which a first through hole is formed through a peripheral wall of a portion of said tube extending between said first and second slits; second and third through holes are formed through a peripheral wall of said tube at opposite sides of said second slit; and said elongated member is introduced into said tube through said first through hole, extends outwardly from said tube through said second through hole, and is introduced into said tube through said third through hole.

10. A length-measuring device according to claim 9, in which said first and second through holes are formed through said peripheral wall of said portion of said tube extending between said first and second slits in such a manner that said elongated member passes through said first and second through holes so as not to intersect the center of said tube.

11. A length-measuring device according to claim 2, in which said pulling means is connected at its proximal end, opposite said one ends to said tube.

12. A length-measuring device according to claim 11, in which said pulling means comprises an elongated member one end of which comprises said one end of said pulling means and has a connecting relation with said length-measuring portion, said elongated member being introduced into said tube from a portion of said tube other than said length-measuring portion.

13. A length-measuring device according to claim 12, in which said pulling means further comprises a spring member which is connected at one end to a proximal end of said elongated member opposite said one end of said elongated member and is connected at the other end to said tube, the pulling force of said pulling means being a contracting force of said spring member.

14. A length-measuring device according to claim 12, in which said elongated member is introduced into said tube through said second slit.

15. A length-measuring device according to claim 12, in which a first through hole is formed through a peripheral wall of a portion of said tube extending between said first and second slits; second and third through holes are formed through a peripheral wall of said tube at opposite sides of said second slit; and said elongated member is introduced into said tube through said first through hole, extends outwardly from said tube through said second through hole, and is introduced into said tube through said third through hole.

16. A length-measuring device according to claim 15, in which said first and second through holes are formed through said peripheral wall of said portion of said tube extending between said first and second slits in such a manner that said elongated member passes through said first and second through holes so as not to intersect the center of said tube.

17. A length-measuring device according to claim 12, in which said elongated member is a wire.

18. A length-measuring device according to claim 11, further comprising a core rod, in which a distal end of said core rod is extended in said tube past said first slit toward said distal end of said tube when said device is not in use, and said core rod is pulled toward a proximal side of said tube to an extent that said distal end of said core rod is moved backward past said second slit when said length-measuring portion is to be pulled.

19. A length-measuring device according to claim 1, in which said bending means comprises a resilient member for bending said tube at said first and second slits by its resilient force.

20. A length-measuring device according to claim 1, in which said first and second slits are displaced from each other circumferentially of said tube.

21. A length-measuring device according to claim 20, in which said first and second slits are displaced from each other at an angle of 180 degrees circumferentially of said tube.

22. A length-measuring device according to claim 20, in which said first and second slits are displaced from each other at an angle of 90 degrees circumferentially of said tube.

23. A length-measuring device according to claim 1, in which said tube includes chamfered edges in an outer peripheral surface of said tube at said first and second slits.

24. A length-measuring device according to claim 1, in which a distance between said first and second slits is shorter than said length-measuring portion.

25. A length-measuring device according to claim 24, in which said distance between said first and second slits is about a half of a length of said length-measuring portion.

26. A length-measuring device according to claim 1, in which a scale is formed on said length-measuring portion.

27. A length-measuring device according to claim 26, in which another scale is also formed on a portion of said tube extending between said first and second slits, said another scale corresponding to said scale on said length-measuring portion when said tube is bent.

28. A length-measuring device according to claim 26, in which said scale has a plurality of scale marks.

29. A length-measuring device according to claim 28, in which said scale marks have different colors, respectively.

30. A length-measuring device according to claim 1, in which said length-measuring portion includes at least one colored section colored with a reference color for adjusting a color tone of an observed image displayed on a monitor of said endoscope.

31. A length-measuring device according to claim 30, in which said reference color is white.

32. A length-measuring device according to claim 30, in which said length-measuring portion includes a plurality of colored sections comprising blue, green and red colored sections.

33. A length-measuring device according to claim 32, in which said blue, green and red colored sections have the same length.

34. A length-measuring device according to claim 32, in which said red colored section has a smaller length while said blue colored section has a greater length.

35. A length-measuring device according to claim 32, wherein said plurality of colored sections further comprises a white-colored section interposed between said blue, green and red colored sections, and each white colored section has the same length as said blue, green and red colored sections.

36. A length-measuring device according to claim 30, in which a portion of said tube extending between said first and second slits also includes at least one colored section, with each colored section of said portion of said tube extending between said first and second slits being adjacent a similarly colored portion of said length-measuring portion when said tube is bent.

37. A length-measuring device according to claim 36, in which said length-measuring portion and said portion of said tube extending between said first and second slits each include a plurality of colored sections, said plurality of colored sections of said portion of said tube extending between said first and second slits corresponding in color and length to the plurality of colored sections of said length-measuring portion when said tube is bent.

38. A length-measuring device for use with an endoscope, comprising:
 (a) a tube having a first slit formed therein and a second slit formed therein and disposed rearwardly of said first slit, said tube being bendable at each of said first and second slits, and said tube further having a length-measuring portion extending forwardly from said first slit to a distal end of said tube;
 (b) means for bending said tube at said first and second slits; and
 (c) a core rod inserted into said tube from a proximal end of said tube and extending to a position near said distal end of said tube, whereby when said core rod in said tube is passed past said first slit toward said distal end of said tube, said tube can not be bent at said first and second slits, and when said core rod is retracted past said second slit toward said proximal end of said tube, said tube can be bent at said first and second slits.

39. A length-measuring device according to claim 38, further comprising means for limiting retracting movement of said core rod.

40. A length-measuring device according to claim 39, in which said retraction limiting means comprises a stopper mounted on a distal end portion of said core rod, and a constricted portion of said tube having an inner diameter smaller than outer diameter of said stopper.

41. A length-measuring device according to claim 38, further comprising means for stopping said core rod in such a position that the distal end of said core rod is disposed adjacent to and forwardly of said second slit.

42. A length-measuring device according to claim 41, in which said stopping means releaseably stops said core rod.

43. A length-measuring device according to claim 38, further comprising means for urging said core rod in its retracting direction.

44. A length-measuring device according to claim 43, further comprising means for retaining said core rod on said tube with a distal end of said core rod being disposed forwardly of said first slit.

45. A length-measuring device according to claim 44, in which said retaining means comprises a mouthpiece mounted on said proximal end of said tube, and a manipulation thumbpiece which is mounted on a proximal end of said core rod and releaseably engaged with said mouthpiece.

46. A length-measuring device according to claim 43, in which said urging means comprises a spring.

47. A length-measuring device according to claim 46, further comprising a mouthpiece mounted on said proximal end of said tube and a manipulation thumbpiece mounted on a proximal end of said core rod, and wherein said spring is wound in a compressed condition around said core rod and acts between said mouthpiece and manipulation thumbpiece.

48. A length-measuring device for use with an endoscope, comprising:
(a) a first tube having a first slit formed therein and a second slit formed therein and disposed rearwardly of said first slit, said tube being bendable at each of said first and second slits, and said tube further having a length-measuring portion extending forwardly from said first slit to a distal end of said tube;
(b) means for bending said tube at said first and second slits; and
(c) a liquid supply port provided at a proximal end portion of said tube for supplying a liquid such as a cleaning liquid into said tube.

49. A length-measuring device according to claim 48, further comprising an outer tube for covering said first and second slits, said outer tube being detachably mounted on a distal end portion of said first tube.

50. A length-measuring device according to claim 49, in which an opening is formed in said distal end of said first tube.

51. A length-measuring device for use with an endoscope, comprising:
(a) a tube having a first slit formed therein and a second slit formed therein and disposed rearwardly of said first slit, said tube being bendable at each of said first and second slits, and said tube further having a length-measuring portion extending forwardly from said first slit to a distal end of said tube;
(b) means for bending said tube at said first and second slits;
(c) a core rod inserted into said tube from a proximal end of said tube and extending to a position near said distal end of said tube, whereby when said core rod in said tube is moved past said first slit toward said distal end of said tube, said tube can not be bent at said first and second slits, and when said core rod is retracted past said second slit toward said proximal end of said tube, said tube can be bent at said first and second slits; and
(d) a mouthpiece mounted on said proximal end of said tube and having a liquid supply port for supplying a liquid such as a cleaning liquid into said tube, said mouthpiece further having at its proximal end an opening through which said core rod is projected outwardly.

52. A length-measuring device according to claim 51, in which an axis of said opening extends along an axis of said tube, and an axis of said liquid supply port extends in a direction perpendicular to said axis of said tube.

53. A length-measuring device according to claim 51, further comprising a manipulation thumbpiece mounted on a proximal end of said core rod, said manipulation thumbpiece being engageable with said opening in a water-tight manner.

54. A length-measuring device for use with an endoscope, comprising:
(a) a tube having a first slit formed therein and a second slit formed therein and disposed rearwardly of said first slit, said tube being bendable at each of said first and second slits, and said tube further having a length-measuring portion extending forwardly from said first slit to a distal end of said tube;
(b) means for bending said tube at said first and second slits; and
(c) a cut portion being cut through at a position disposed rearwardly of said second slit to divide said tube into two parts, said two parts of said tube being connected together at said cut portion in such a manner that said two parts are rotatable about an axis of said tube.

55. A length-measuring device according to claim 54, in which said tube is transversely cut through.

56. A length-measuring device according to claim 54, in which said two parts of said tube are connected together in a manner to prevent said two parts from being axially moved away from each other.

57. A length-measuring device according to claim 54, in which a pair of connecting pipes are fitted respectively to portions of said tube located immediately adjacent to said cut portion on opposite sides of said cut portion, one of said pair of connecting pipes being fitted into the other in such a manner that said pair of connecting pipes are rotatable relative to each other about said axis of said tube.

58. A length-measuring device according to claim 57, in which said pair of connecting pipes are fitted into insides of said portions of said tube.

59. A length-measuring device according to claim 57, in which one of said pair of connecting pipes has at one end a flange which is engaged with one end of the other of said pair of connecting pipes to prevent said pair of connecting pipes from axially moving away from each other.

60. A length-measuring device according to claim 54, further comprising a core rod inserted into said tube, whereby when said core rod in said tube is moved past said first slit toward said distal end of said tube, said tube can not be bent at said first and second slits, and when said core rod is retracted past said second slit toward said proximal end of said tube, said tube can be bent at said first and second slits; said tube further having a stopper portion for limiting a retracting movement of said core rod, and said cut portion being disposed rearwardly of said stopper portion.

61. A length-measuring device for use with an endoscope, comprising:
(a) a tube having a first slit formed therein and a second slit formed therein and disposed rearwardly of said first slit, said tube being bendable at each of said first and second slits, and said tube further having a length-measuring portion extending forwardly from said first slit to a distal end of said tube; and (b) means for bending said tube at said first and second slits; and (c) a divided portion being cut through at a position disposed rearwardly of said second slit to divide said tube into a proximal portion and a distal portion, said proximal and distal portions of said tube being releaseably connected together at said divided portion.

62. A length-measuring device according to claim 61, in which said tube is transversely cut through at said divided portion.

63. A length-measuring device according to claim 61, in which a pair of connecting pipes are fitted respectively to portions of said tube located immediately adjacent to said divided portion on opposite sides of said divided portion, said pair of connecting pipes being releaseably connected together to join said proximal and distal portions of said tube together.

64. A length-measuring device according to claim 63, further comprising a connecting pipe fitted into insides of said portions of said tube.

65. A length-measuring device according to claim 63, in which said pair of connecting pipes are threadedly connected together.

66. A length-measuring device according to claim 61, in which said bending means comprises a resilient member having a proximal end fixedly secured to said tube, and pulling said length-measuring portion toward said second slit by a resilient force thereof, said divided portion being disposed rearwardly of said proximal end of said resilient member.

67. A length-measuring device according to claim 66, further comprising a connecting pipe fitted to said tube at said divided portion, said proximal end of said resilient member being fixedly secured to said connecting pipe.

68. A length-measuring device according to one of claims 1, 38, 48, 51, 54 and 61, in which said tube is flexible.

69. A reference color display device for color adjustment for use with an endoscope, comprising:

a tube having a distal portion which can be bent from a straight condition to a generally T-shaped condition by a remote manipulation from a proximal side of said tube, said distal portion having at least one colored section colored in a reference color for adjusting a color tone of an image picked up by said endoscope and displayed on a monitor of said endoscope.

70. A reference color display device according to claim 69, in which said reference color is white.

71. A reference color display device according to claim 69, in which said distal portion includes a plurality of colored sections comprising blue, green and red colored sections.

72. A reference color display device according to claim 71, in which said plurality of colored sections have the same length.

73. A reference color display device according to claim 71, in which said red colored section has a smaller length, while said blue colored section has a greater length.

74. A reference color display device according to claim 71, wherein said plurality of colored sections further comprises a white colored section interposed between said blue, green and red colored sections, and each white colored section has the same length as said blue, green and red colored sections.

75. A reference color display device according to claim 69, in which said tube has a first slit formed therein and a second slit formed therein and disposed rearwardly of said first slit, said tube being bendable at each of said first and second slits, said distal portion corresponding to a portion of said tube extending from said first slit to the distal end of said tube.

76. A reference color display device according to claim 75, in which a portion of said tube extending between said first and second slits also includes at least one colored section, with each colored section of said portion of said tube extending between said first and second slits being adjacent a similarly colored section of said distal portion when said tube is bent.

77. A reference color display device according to claim 69, in which said tube is flexible.

* * * * *